(12) United States Patent
Buchberger

(10) Patent No.: US 12,089,640 B2
(45) Date of Patent: Sep. 17, 2024

(54) INHALER COMPONENT

(71) Applicant: NICOVENTURES TRADING LIMITED, London (GB)

(72) Inventor: Helmut Buchberger, Ennsdorf (AT)

(73) Assignee: NICOVENTURES TRADING LIMITED, London (GB)

( * ) Notice: Subject to any disclaimer, the term of this patent is extended or adjusted under 35 U.S.C. 154(b) by 0 days.

(21) Appl. No.: 17/248,137

(22) Filed: Jan. 11, 2021

(65) Prior Publication Data
US 2021/0204602 A1 Jul. 8, 2021

Related U.S. Application Data

(63) Continuation of application No. 15/997,113, filed on Jun. 4, 2018, now Pat. No. 10,918,820, which is a
(Continued)

(30) Foreign Application Priority Data

Feb. 11, 2011 (AT) .................................. A 187/2011
Jul. 27, 2011 (AT) ................................. A 1095-2011

(51) Int. Cl.
*A61M 11/04* (2006.01)
*A24F 40/44* (2020.01)
(Continued)

(52) U.S. Cl.
CPC ............... *A24F 40/46* (2020.01); *A24F 40/44* (2020.01); *A61M 11/041* (2013.01);
(Continued)

(58) Field of Classification Search
CPC .......... A61M 11/04–042; A61M 15/00; A61M 15/0021; A61M 15/06; A61M 16/1075; A61M 16/14; A61M 16/20–201
See application file for complete search history.

(56) References Cited

U.S. PATENT DOCUMENTS 228,598 A 6/1880 Buckley
353,327 A 11/1886 Randolph
(Continued)

FOREIGN PATENT DOCUMENTS

AT 16602008 10/2008
AT 507187 A4 3/2010
(Continued)

OTHER PUBLICATIONS

Aerosols, "Pulmonary Pharmacology: Delivery Devices and Medications," Sep. 6, 2017, available at www.cdeu.org/cecourses/z98207/ch4.html, 2 pages.
(Continued)

*Primary Examiner* — Rachel T Sippel
(74) *Attorney, Agent, or Firm* — Husch Blackwell

(57) ABSTRACT

The invention relates to an inhaler component for forming a vapor-air mixture and/or condensation aerosol by vaporizing a liquid material and optionally condensing the vapor formed, including: a heating element for vaporizing a portion of the liquid material; a wick for automatically supplying the liquid material to the heating element, wherein the wick comprises at least two end sections arranged apart from each other; a first capillary gap for automatically supplying the liquid material to the wick, wherein a first end section of the wick projects into the first capillary gap. In order that the heating element can be supplied more quickly and more reliably with the liquid material, a second capillary gap is provided, which receives therein the second end section of the wick.

9 Claims, 8 Drawing Sheets

Related U.S. Application Data continuation of application No. 14/268,909, filed on May 2, 2014, now Pat. No. 10,010,695, which is a continuation of application No. 13/984,512, filed as application No. PCT/AT2012/000017 on Feb. 2, 2012, now Pat. No. 8,752,545.

(51) Int. Cl.

| | | |
|---|---|---|
| *A24F 40/46* | (2020.01) | |
| *A61M 15/00* | (2006.01) | |
| *A61M 15/06* | (2006.01) | |
| *A61M 16/10* | (2006.01) | |
| *A61M 16/14* | (2006.01) | |
| *B05B 7/00* | (2006.01) | |
| *B05B 7/16* | (2006.01) | |
| *H05K 1/02* | (2006.01) | |
| *A24F 40/10* | (2020.01) | |
| *A61M 15/08* | (2006.01) | |

(52) U.S. Cl.
CPC .......... *A61M 11/042* (2014.02); *A61M 15/00* (2013.01); *A61M 15/0021* (2014.02); *A61M 15/06* (2013.01); *A61M 16/1075* (2013.01); *A61M 16/109* (2014.02); *A61M 16/14* (2013.01); *A61M 16/145* (2014.02); *B05B 7/0012* (2013.01); *B05B 7/168* (2013.01); *B05B 7/1686* (2013.01); *H05K 1/0272* (2013.01); *A24F 40/10* (2020.01); *A61M 15/08* (2013.01); *A61M 2205/3606* (2013.01); *A61M 2205/3653* (2013.01); *A61M 2205/8206* (2013.01); *H05K 1/0298* (2013.01)

(56) References Cited

U.S. PATENT DOCUMENTS

| | | |
|---|---|---|
| 576,653 A | 2/1897 | Bowlby |
| 595,070 A | 12/1897 | Oldenbusch |
| 744,074 A | 11/1903 | Hiering |
| 799,844 A | 9/1905 | Fuller |
| 885,374 A | 4/1908 | Pohlig |
| 1,163,183 A | 12/1915 | Stoll |
| D53,386 S | 5/1919 | Joseph |
| 1,436,157 A | 11/1922 | Fazio |
| 1,807,936 A | 6/1931 | Saunders |
| 1,815,069 A | 7/1931 | Petro |
| 1,937,120 A | 11/1933 | Julius et al. |
| 1,937,987 A | 12/1933 | Sexton |
| 2,057,353 A | 10/1936 | Whittemore |
| 2,262,318 A | 11/1941 | Fox |
| 2,371,006 A | 3/1945 | Weaver |
| 2,411,946 A | 12/1946 | Max et al. |
| 2,467,923 A | 4/1949 | Allen |
| 2,483,304 A | 9/1949 | Rudolf et al. |
| 2,522,952 A | 9/1950 | Joseph et al. |
| 2,658,368 A | 11/1953 | Siegel |
| 2,782,910 A | 2/1957 | Saul et al. |
| 2,809,634 A | 10/1957 | Hirotada et al. |
| 3,080,624 A * | 3/1963 | Weber, III ................ A61L 9/03 261/142 |
| 3,111,396 A | 11/1963 | Ball |
| 3,165,225 A | 1/1965 | Georg et al. |
| 3,221,752 A | 12/1965 | Strahm |
| 3,402,724 A | 9/1968 | Blount et al. |
| 3,431,393 A | 3/1969 | Katsuda et al. |
| 3,433,632 A | 3/1969 | Elbert et al. |
| 3,490,718 A | 1/1970 | Vary et al. |
| 3,496,336 A | 2/1970 | Hingorany et al. |
| 3,521,643 A | 7/1970 | Toth et al. |
| 3,604,428 A | 9/1971 | Moukaddem |
| 3,722,742 A | 3/1973 | Wertz |
| 3,743,136 A | 7/1973 | Chambers |
| 3,804,100 A | 4/1974 | Fariello |
| 3,861,523 A | 1/1975 | Fountain et al. |
| 3,863,803 A | 2/1975 | Valcic |
| 3,915,145 A | 10/1975 | Tomita |
| 3,964,902 A | 6/1976 | Fletcher et al. |
| 4,009,713 A | 3/1977 | Simmons et al. |
| 4,031,906 A | 6/1977 | Knapp |
| 4,094,119 A | 6/1978 | Sullivan |
| 4,117,850 A | 10/1978 | Wood |
| 4,145,001 A | 3/1979 | Weyenberg et al. |
| 4,161,283 A | 7/1979 | Hyman |
| 4,190,412 A | 2/1980 | Nitta |
| 4,193,513 A | 3/1980 | Bull, Jr. |
| 4,214,658 A | 7/1980 | Crow |
| 4,253,476 A | 3/1981 | Sato |
| 4,449,039 A | 5/1984 | Fukazawa et al. |
| 4,503,851 A | 3/1985 | Braunroth |
| D279,508 S | 7/1985 | Bauer et al. |
| 4,579,858 A | 4/1986 | Ferno et al. |
| 4,588,976 A | 5/1986 | Jaselli |
| 4,597,961 A | 7/1986 | Etscorn |
| 4,655,231 A | 4/1987 | Ray et al. |
| 4,676,237 A | 6/1987 | Wood et al. |
| 4,677,992 A | 7/1987 | Bliznak |
| 4,733,794 A | 3/1988 | Kent |
| 4,735,217 A | 4/1988 | Gerth et al. |
| 4,736,755 A | 4/1988 | Oldham et al. |
| 4,753,383 A | 6/1988 | Focke et al. |
| 4,793,478 A | 12/1988 | Tudor |
| 4,830,028 A | 5/1989 | Lawson et al. |
| 4,848,374 A | 7/1989 | Chard et al. |
| 4,858,630 A | 8/1989 | Banerjee et al. |
| 4,878,832 A | 11/1989 | Lynch |
| 4,885,129 A | 12/1989 | Leonard et al. |
| 4,917,301 A | 4/1990 | Munteanu |
| 4,922,901 A | 5/1990 | Brooks et al. |
| 4,923,052 A | 5/1990 | Englebert |
| 4,923,059 A | 5/1990 | Evers et al. |
| 4,924,888 A | 5/1990 | Perfetti et al. |
| 4,947,874 A | 8/1990 | Brooks et al. |
| 4,947,875 A | 8/1990 | Brooks et al. |
| 4,961,438 A | 10/1990 | Korte |
| 4,978,814 A | 12/1990 | Honour |
| 5,027,837 A | 7/1991 | Clearman et al. |
| 5,031,646 A | 7/1991 | Lippiello et al. |
| 5,044,550 A | 9/1991 | Lamm |
| 5,046,514 A | 9/1991 | Bolt |
| 5,060,671 A | 10/1991 | Counts et al. |
| D322,687 S | 12/1991 | Tschudin |
| 5,095,647 A | 3/1992 | Zobele et al. |
| 5,095,921 A | 3/1992 | Losee et al. |
| 5,096,921 A | 3/1992 | Bollinger et al. |
| 5,099,861 A | 3/1992 | Clearman et al. |
| 5,121,881 A | 6/1992 | Lembeck |
| 5,167,242 A | 12/1992 | Turner et al. |
| 5,179,966 A | 1/1993 | Losee et al. |
| 5,234,008 A | 8/1993 | Fagg |
| 5,247,947 A | 9/1993 | Clearman et al. |
| 5,269,327 A | 12/1993 | Counts et al. |
| D346,878 S | 5/1994 | Gee et al. |
| 5,322,075 A | 6/1994 | Deevi et al. |
| 5,357,271 A | 10/1994 | Wiklof et al. |
| 5,388,574 A | 2/1995 | Ingebrethsen |
| 5,390,864 A | 2/1995 | Alexander |
| 5,404,890 A | 4/1995 | Gentry et al. |
| 5,408,574 A | 4/1995 | Deevi et al. |
| 5,448,317 A | 9/1995 | Huang |
| 5,479,948 A | 1/1996 | Counts et al. |
| 5,497,792 A | 3/1996 | Prasad et al. |
| 5,501,236 A | 3/1996 | Hill et al. |
| 5,505,214 A | 4/1996 | Collins et al. |
| 5,530,225 A | 6/1996 | Hajaligol |
| 5,540,241 A | 7/1996 | Kim |
| 5,553,791 A | 9/1996 | Alexander |
| 5,568,819 A | 10/1996 | Gentry et al. |
| 5,626,866 A | 5/1997 | Ebert et al. |
| 5,636,787 A | 6/1997 | Gowhari |
| 5,649,554 A | 7/1997 | Sprinkel et al. |
| 5,659,656 A | 8/1997 | Das |
| 5,666,977 A | 9/1997 | Higgins et al. |

(56) References Cited

U.S. PATENT DOCUMENTS

| | | |
|---|---|---|
| 5,692,291 A | 12/1997 | Deevi et al. |
| D392,069 S | 3/1998 | Rowland |
| 5,743,251 A | 4/1998 | Howell et al. |
| D404,201 S | 1/1999 | Wennerstrom |
| 5,865,185 A | 2/1999 | Collins et al. |
| 5,875,968 A | 3/1999 | Miller et al. |
| 5,878,722 A | 3/1999 | Gras et al. |
| 5,878,752 A | 3/1999 | Adams et al. |
| 5,894,841 A | 4/1999 | Voges |
| 5,896,984 A | 4/1999 | Focke et al. |
| D414,892 S | 10/1999 | Chen |
| 5,967,312 A | 10/1999 | Jacobs |
| 6,040,560 A | 3/2000 | Fleischhauer et al. |
| 6,058,711 A | 5/2000 | Maciaszek et al. |
| 6,065,592 A | 5/2000 | Wik |
| 6,095,505 A | 8/2000 | Miller |
| 6,119,684 A | 9/2000 | Noehl et al. |
| D432,263 S | 10/2000 | Issa |
| D434,217 S | 11/2000 | Packard et al. |
| D434,979 S | 12/2000 | Liu |
| 6,155,268 A | 12/2000 | Takeuchi |
| D436,725 S | 1/2001 | Rogers |
| D438,003 S | 2/2001 | Minagawa et al. |
| D441,133 S | 4/2001 | Emery |
| 6,275,650 B1 | 8/2001 | Lambert |
| D449,521 S | 10/2001 | Pinkus et al. |
| 6,321,757 B1 | 11/2001 | McCutcheon |
| 6,446,793 B1 | 9/2002 | Layshock |
| D466,012 S | 11/2002 | Baker |
| D470,765 S | 2/2003 | Baker |
| D471,804 S | 3/2003 | Staples |
| D472,012 S | 3/2003 | South |
| 6,527,166 B1 | 3/2003 | Focke et al. |
| 6,530,495 B1 | 3/2003 | Joseph |
| 6,561,391 B1 | 5/2003 | Baker |
| 6,652,804 B1 | 11/2003 | Neumann et al. |
| 6,681,998 B2 | 1/2004 | Sharpe et al. |
| 6,701,921 B2 | 3/2004 | Sprinkel, Jr. et al. |
| 6,715,605 B1 | 4/2004 | Manservigi et al. |
| D493,617 S | 8/2004 | Armato |
| 6,790,496 B1 | 9/2004 | Levander et al. |
| 6,799,576 B2 | 10/2004 | Farr |
| 6,830,046 B2 | 12/2004 | Blakley et al. |
| D509,732 S | 9/2005 | Staples |
| 7,100,618 B2 | 9/2006 | Dominguez |
| 7,112,712 B1 | 9/2006 | Ancell |
| D545,186 S | 6/2007 | Liebe et al. |
| D549,573 S | 8/2007 | Liebe et al. |
| 7,253,282 B2 | 8/2007 | Dehmlow et al. |
| 7,263,228 B2 | 8/2007 | Mori |
| 7,263,282 B2 * | 8/2007 | Meyer .................. H05B 3/28 |
| | | 392/394 |
| D550,455 S | 9/2007 | Barnhart |
| D566,329 S | 4/2008 | Bagaric et al. |
| D566,890 S | 4/2008 | Bagaric et al. |
| 7,389,878 B1 | 6/2008 | Torrico |
| D573,889 S | 7/2008 | Short et al. |
| 7,400,940 B2 | 7/2008 | McRae et al. |
| D575,451 S | 8/2008 | Jones et al. |
| 7,455,176 B2 | 11/2008 | Focke, et al. |
| 7,540,286 B2 | 6/2009 | Cross et al. |
| 7,565,969 B2 | 7/2009 | He |
| 7,575,002 B2 | 8/2009 | Demars et al. |
| D606,854 S | 12/2009 | Greenhalgh |
| D610,983 S | 3/2010 | Wai |
| D611,806 S | 3/2010 | Bried |
| D613,903 S | 4/2010 | Wu et al. |
| D613,904 S | 4/2010 | Wu et al. |
| D616,753 S | 6/2010 | Beam et al. |
| 7,726,320 B2 | 6/2010 | Robinson et al. |
| 7,767,698 B2 | 8/2010 | Warchol et al. |
| 7,832,410 B2 | 11/2010 | Hon |
| D628,469 S | 12/2010 | Taylor et al. |
| D631,838 S | 2/2011 | Cheng |
| D636,257 S | 4/2011 | Bougoulas et al. |
| 7,992,554 B2 | 8/2011 | Radomski et al. |
| D649,658 S | 11/2011 | Belfance et al. |
| D650,738 S | 12/2011 | Leung |
| 8,079,371 B2 | 12/2011 | Robinson et al. |
| 8,113,343 B2 | 2/2012 | Åkerlind |
| D656,094 S | 3/2012 | Wu |
| 8,156,944 B2 | 4/2012 | Han |
| D661,016 S | 5/2012 | Borges et al. |
| D671,677 S | 11/2012 | Wu |
| D671,678 S | 11/2012 | Wu |
| 8,307,834 B1 | 11/2012 | Palmerino, Sr. et al. |
| D672,642 S | 12/2012 | Supranowicz |
| D674,539 S | 1/2013 | Wu |
| 8,365,742 B2 | 2/2013 | Hon |
| 8,375,957 B2 | 2/2013 | Hon |
| 8,393,331 B2 | 3/2013 | Hon |
| 8,430,106 B2 | 4/2013 | Potter et al. |
| 8,448,783 B2 | 5/2013 | Vecchi |
| 8,490,628 B2 | 7/2013 | Hon |
| 8,511,318 B2 | 8/2013 | Hon |
| D693,055 S | 11/2013 | Manca et al. |
| D700,397 S | 2/2014 | Manca et al. |
| 8,689,805 B2 | 4/2014 | Hon |
| 8,752,545 B2 | 6/2014 | Buchberger |
| 8,794,245 B1 | 8/2014 | Scatterday |
| 8,833,364 B2 | 9/2014 | Buchberger |
| D715,760 S | 10/2014 | Kim et al. |
| D716,267 S | 10/2014 | Kim et al. |
| 8,869,793 B1 | 10/2014 | Spandorfer et al. |
| 8,910,640 B2 | 12/2014 | Sears et al. |
| D720,884 S | 1/2015 | Liu |
| 8,948,578 B2 | 2/2015 | Buchberger |
| D723,738 S | 3/2015 | Liu |
| 8,967,155 B2 | 3/2015 | Bundren et al. |
| 8,997,753 B2 | 4/2015 | Li et al. |
| 9,055,617 B2 | 6/2015 | Thorens et al. |
| D736,460 S | 8/2015 | McKeon et al. |
| D737,507 S | 8/2015 | Liu |
| 9,215,895 B2 | 12/2015 | Bowen et al. |
| 9,609,894 B2 | 4/2017 | Abramov et al. |
| 9,623,205 B2 | 4/2017 | Buchberger |
| 9,730,276 B2 | 8/2017 | Vissa et al. |
| 9,943,108 B2 | 4/2018 | Lord |
| 9,961,939 B2 | 5/2018 | Reevell |
| 9,974,335 B2 | 5/2018 | Lord |
| 9,974,743 B2 | 5/2018 | Rose et al. |
| 9,986,760 B2 | 6/2018 | Macko et al. |
| 10,010,695 B2 | 7/2018 | Buchberger |
| 10,045,562 B2 | 8/2018 | Buchberger |
| 10,278,421 B2 | 5/2019 | Lord |
| 10,368,582 B2 | 8/2019 | Lord |
| 10,765,147 B2 | 9/2020 | Buchberger et al. |
| 11,044,937 B2 | 6/2021 | Mcadam et al. |
| 2001/0004934 A1 | 6/2001 | Yamamoto et al. |
| 2001/0042546 A1 | 11/2001 | Umeda et al. |
| 2002/0005207 A1 | 1/2002 | Wrenn et al. |
| 2002/0016370 A1 | 2/2002 | Shytle et al. |
| 2002/0059939 A1 | 5/2002 | Fox |
| 2002/0079309 A1 | 6/2002 | Cox et al. |
| 2003/0005620 A1 | 1/2003 | Ananth et al. |
| 2003/0049025 A1 | 3/2003 | Neumann et al. |
| 2003/0056791 A1 | 3/2003 | Nichols et al. |
| 2003/0064340 A1 | 4/2003 | Pappas |
| 2003/0079309 A1 | 5/2003 | Vandenbelt et al. |
| 2003/0106551 A1 | 6/2003 | Sprinkel et al. |
| 2003/0106552 A1 | 6/2003 | Sprinkel, Jr. et al. |
| 2003/0108342 A1 | 6/2003 | Sherwood et al. |
| 2003/0108743 A1 | 6/2003 | Anderson |
| 2003/0136399 A1* | 7/2003 | Foley .................. A61M 11/002 |
| | | 128/200.14 |
| 2003/0136404 A1 | 7/2003 | Hindle et al. |
| 2003/0168057 A1 | 9/2003 | Snyder et al. |
| 2003/0176467 A1 | 9/2003 | Andersson et al. |
| 2003/0192540 A1 | 10/2003 | Myrman et al. |
| 2003/0200964 A1 | 10/2003 | Blakley et al. |
| 2003/0202169 A1 | 10/2003 | Liu |
| 2004/0025865 A1 | 2/2004 | Nichols et al. |
| 2004/0031485 A1 | 2/2004 | Rustad et al. |
| 2004/0056651 A1 | 3/2004 | Marietta Bersana |

(56) References Cited

U.S. PATENT DOCUMENTS

| | | |
|---|---|---|
| 2004/0081624 A1 | 4/2004 | Nguyen et al. |
| 2004/0129793 A1 | 7/2004 | Nguyen et al. |
| 2004/0198818 A1 | 10/2004 | Quallich et al. |
| 2004/0210151 A1 | 10/2004 | Tsukashima et al. |
| 2004/0213744 A1 | 10/2004 | Lulla et al. |
| 2004/0223917 A1 | 11/2004 | Hindle et al. |
| 2004/0226568 A1 | 11/2004 | Takeuchi et al. |
| 2004/0255941 A1 | 12/2004 | Nichols et al. |
| 2004/0261487 A1 | 12/2004 | Chen |
| 2005/0009870 A1 | 1/2005 | Sher et al. |
| 2005/0016550 A1 | 1/2005 | Katase |
| 2005/0063686 A1 | 3/2005 | Whittle et al. |
| 2005/0087460 A1 | 4/2005 | Bruhn et al. |
| 2005/0133049 A1 | 6/2005 | Fournier et al. |
| 2005/0145260 A1 | 7/2005 | Inagaki et al. |
| 2005/0155985 A1 | 7/2005 | Meyer |
| 2005/0194013 A1 | 9/2005 | Wright |
| 2005/0204799 A1 | 9/2005 | Koch |
| 2005/0211243 A1 | 9/2005 | Esser |
| 2005/0224375 A1 | 10/2005 | Focke et al. |
| 2005/0235991 A1 | 10/2005 | Nichols et al. |
| 2005/0247436 A1 | 11/2005 | Hsu |
| 2005/0268911 A1 | 12/2005 | Cross et al. |
| 2006/0018840 A1 | 1/2006 | Lechuga-Ballesteros et al. |
| 2006/0073182 A1 | 4/2006 | Wong et al. |
| 2006/0078477 A1 | 4/2006 | Althouse et al. |
| 2006/0095311 A1 | 5/2006 | Thompson |
| 2006/0137681 A1 | 6/2006 | Von Hollen et al. |
| 2006/0180143 A1 | 8/2006 | Lind et al. |
| 2006/0196518 A1 | 9/2006 | Hon |
| 2006/0283468 A1 | 12/2006 | Lipowicz |
| 2007/0014549 A1 | 1/2007 | Demarest et al. |
| 2007/0045288 A1 | 3/2007 | Nelson |
| 2007/0062548 A1 | 3/2007 | Horstmann et al. |
| 2007/0074722 A1 | 4/2007 | Giroux et al. |
| 2007/0076067 A1 | 4/2007 | Hamano et al. |
| 2007/0082038 A1 | 4/2007 | Gale et al. |
| 2007/0102013 A1 | 5/2007 | Adams et al. |
| 2007/0107879 A1 | 5/2007 | Radomski et al. |
| 2007/0134169 A1 | 6/2007 | Rabinoff |
| 2007/0135461 A1 | 6/2007 | Rodgers et al. |
| 2007/0144514 A1 | 6/2007 | Yeates et al. |
| 2007/0155255 A1 | 7/2007 | Galauner et al. |
| 2007/0193895 A1 | 8/2007 | Weiss et al. |
| 2007/0267031 A1 | 11/2007 | Hon |
| 2007/0267032 A1 | 11/2007 | Shan |
| 2007/0280972 A1 | 12/2007 | Zhang et al. |
| 2008/0017204 A1 | 1/2008 | Braunshteyn et al. |
| 2008/0092912 A1 | 4/2008 | Robinson et al. |
| 2008/0138423 A1 | 6/2008 | Gonda |
| 2008/0149118 A1 | 6/2008 | Oglesby et al. |
| 2008/0156326 A1 | 7/2008 | Belcastro et al. |
| 2008/0216828 A1 | 9/2008 | Wensley et al. |
| 2008/0223382 A1 | 9/2008 | Zeanah |
| 2008/0228214 A1 | 9/2008 | Hoan et al. |
| 2008/0241255 A1 | 10/2008 | Rose et al. |
| 2008/0302375 A1 | 12/2008 | Andersson et al. |
| 2009/0009534 A1 | 1/2009 | Perani et al. |
| 2009/0023819 A1 | 1/2009 | Axelsson |
| 2009/0050139 A1 | 2/2009 | Watanabe et al. |
| 2009/0090472 A1 | 4/2009 | Radomski |
| 2009/0095311 A1 | 4/2009 | Han |
| 2009/0095312 A1 | 4/2009 | Herbrich et al. |
| 2009/0133691 A1 | 5/2009 | Yamada et al. |
| 2009/0188490 A1 | 7/2009 | Han |
| 2009/0220222 A1 | 9/2009 | Rabin et al. |
| 2009/0241947 A1 | 10/2009 | Bedini et al. |
| 2009/0266837 A1 | 10/2009 | Gelardi et al. |
| 2009/0272379 A1 | 11/2009 | Thorens et al. |
| 2009/0288966 A1 | 11/2009 | Minarelli et al. |
| 2009/0293892 A1 | 12/2009 | Williams et al. |
| 2009/0324206 A1 | 12/2009 | Young et al. |
| 2010/0003904 A1 | 1/2010 | Duescher |
| 2010/0006113 A1 | 1/2010 | Urtsev et al. |
| 2010/0039066 A1 | 2/2010 | Yuan et al. |
| 2010/0059070 A1 | 3/2010 | Potter et al. |
| 2010/0065653 A1 | 3/2010 | Wingo et al. |
| 2010/0083959 A1 | 4/2010 | Siller |
| 2010/0108059 A1 | 5/2010 | Axelsson et al. |
| 2010/0116691 A1 | 5/2010 | Papadimitrakopoulos et al. |
| 2010/0181387 A1 | 7/2010 | Zaffaroni et al. |
| 2010/0182608 A1 | 7/2010 | Zribi et al. |
| 2010/0200006 A1 | 8/2010 | Robinson et al. |
| 2010/0211011 A1 | 8/2010 | Haar |
| 2010/0236546 A1 | 9/2010 | Yamada et al. |
| 2010/0242974 A1 | 9/2010 | Pan |
| 2010/0260688 A1 | 10/2010 | Warchol et al. |
| 2010/0313901 A1 | 12/2010 | Fernando et al. |
| 2011/0011396 A1 | 1/2011 | Fang |
| 2011/0036363 A1 | 2/2011 | Urtsev et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0180433 A1 | 7/2011 | Rennecamp |
| 2011/0192914 A1 | 8/2011 | Ishigami |
| 2011/0209717 A1 | 9/2011 | Han |
| 2011/0226236 A1 | 9/2011 | Buchberger |
| 2011/0268809 A1 | 11/2011 | Brinkley et al. |
| 2011/0274628 A1 | 11/2011 | Borschke |
| 2011/0277757 A1 | 11/2011 | Terry et al. |
| 2011/0278189 A1 | 11/2011 | Terry et al. |
| 2011/0290267 A1 | 12/2011 | Yamada et al. |
| 2011/0297166 A1 | 12/2011 | Takeuchi et al. |
| 2011/0303231 A1 | 12/2011 | Li et al. |
| 2011/0309157 A1 | 12/2011 | Yang et al. |
| 2012/0111347 A1 | 5/2012 | Hon |
| 2012/0145169 A1 | 6/2012 | Wu |
| 2012/0180994 A1 | 7/2012 | Yang et al. |
| 2012/0180995 A1 | 7/2012 | Yang et al. |
| 2012/0199146 A1 | 8/2012 | Marangos |
| 2012/0227752 A1 | 9/2012 | Alelov |
| 2012/0227753 A1 | 9/2012 | Newton |
| 2012/0242974 A1 | 9/2012 | LaValley et al. |
| 2012/0255567 A1 | 10/2012 | Rose et al. |
| 2012/0260927 A1 | 10/2012 | Liu |
| 2012/0285476 A1 | 11/2012 | Hon |
| 2013/0074857 A1 | 3/2013 | Buchberger |
| 2013/0081623 A1 | 4/2013 | Buchberger |
| 2013/0081642 A1 | 4/2013 | Safari |
| 2013/0087160 A1 | 4/2013 | Gherghe |
| 2013/0098786 A1 | 4/2013 | Collins |
| 2013/0112214 A1 | 5/2013 | Bundren et al. |
| 2013/0142782 A1 | 6/2013 | Rahmel et al. |
| 2013/0192615 A1 | 8/2013 | Tucker et al. |
| 2013/0192619 A1 | 8/2013 | Tucker et al. |
| 2013/0192620 A1 | 8/2013 | Tucker et al. |
| 2013/0192621 A1 | 8/2013 | Li et al. |
| 2013/0192623 A1 | 8/2013 | Tucker et al. |
| 2013/0213419 A1 | 8/2013 | Tucker et al. |
| 2013/0228191 A1 | 9/2013 | Newton |
| 2013/0255702 A1 | 10/2013 | Griffith, Jr. et al. |
| 2013/0284192 A1 | 10/2013 | Peleg et al. |
| 2013/0298905 A1 | 11/2013 | Levin et al. |
| 2013/0306084 A1 | 11/2013 | Flick |
| 2013/0319407 A1 | 12/2013 | Liu |
| 2013/0319435 A1 | 12/2013 | Flick |
| 2013/0333700 A1 | 12/2013 | Buchberger |
| 2013/0340779 A1 | 12/2013 | Liu |
| 2013/0341218 A1 | 12/2013 | Liu |
| 2013/0342157 A1 | 12/2013 | Liu |
| 2014/0000638 A1 | 1/2014 | Sebastian et al. |
| 2014/0007863 A1 | 1/2014 | Chen |
| 2014/0007892 A1 | 1/2014 | Liu |
| 2014/0018840 A1 | 1/2014 | Morgan et al. |
| 2014/0020697 A1 | 1/2014 | Liu |
| 2014/0023824 A1 | 1/2014 | Masanek et al. |
| 2014/0048086 A1 | 2/2014 | Zhanghua |
| 2014/0053831 A1 | 2/2014 | Leamon et al. |
| 2014/0060528 A1 | 3/2014 | Liu |
| 2014/0060554 A1 | 3/2014 | Collett et al. |
| 2014/0060555 A1 | 3/2014 | Chang et al. |
| 2014/0064715 A1 | 3/2014 | Greim et al. |

(56) References Cited

U.S. PATENT DOCUMENTS

| | | |
|---|---|---|
| 2014/0106155 A1 | 4/2014 | Iandoli Espinosa |
| 2014/0123989 A1 | 5/2014 | LaMothe |
| 2014/0166027 A1 | 6/2014 | Fuisz et al. |
| 2014/0182608 A1 | 7/2014 | Egoyants et al. |
| 2014/0196717 A1 | 7/2014 | Liu |
| 2014/0196731 A1 | 7/2014 | Scatterday |
| 2014/0202454 A1 | 7/2014 | Buchberger |
| 2014/0202476 A1 | 7/2014 | Egoyants et al. |
| 2014/0209105 A1 | 7/2014 | Sears et al. |
| 2014/0216485 A1 | 8/2014 | Egoyants et al. |
| 2014/0238396 A1 | 8/2014 | Buchberger |
| 2014/0238422 A1 | 8/2014 | Plunkett et al. |
| 2014/0238423 A1 | 8/2014 | Tucker et al. |
| 2014/0238424 A1 | 8/2014 | Macko et al. |
| 2014/0253144 A1 | 9/2014 | Novak et al. |
| 2014/0261486 A1 | 9/2014 | Potter et al. |
| 2014/0261487 A1 | 9/2014 | Chapman et al. |
| 2014/0261488 A1 | 9/2014 | Tucker |
| 2014/0261489 A1 | 9/2014 | Cadieux et al. |
| 2014/0261490 A1 | 9/2014 | Kane |
| 2014/0261493 A1 | 9/2014 | Smith et al. |
| 2014/0261495 A1 | 9/2014 | Novak, III et al. |
| 2014/0270726 A1 | 9/2014 | Egoyants et al. |
| 2014/0270729 A1 | 9/2014 | Depiano et al. |
| 2014/0270730 A1 | 9/2014 | DePiano et al. |
| 2014/0283825 A1 | 9/2014 | Buchberger |
| 2014/0286630 A1 | 9/2014 | Buchberger |
| 2014/0299125 A1 | 10/2014 | Buchberger |
| 2014/0299141 A1 | 10/2014 | Flick |
| 2014/0305431 A1 | 10/2014 | Holley et al. |
| 2014/0332019 A1 | 11/2014 | Liu |
| 2014/0338680 A1 | 11/2014 | Abramov et al. |
| 2014/0345635 A1 | 11/2014 | Rabinowitz et al. |
| 2015/0020823 A1 | 1/2015 | Lipowicz et al. |
| 2015/0101626 A1 | 4/2015 | Li et al. |
| 2015/0114411 A1 | 4/2015 | Buchberger |
| 2015/0128964 A1 | 5/2015 | Bundren et al. |
| 2015/0128971 A1 | 5/2015 | Verleur et al. |
| 2015/0136756 A1 | 5/2015 | Vissa et al. |
| 2015/0157055 A1 | 6/2015 | Lord |
| 2015/0164143 A1 | 6/2015 | Maas |
| 2015/0181934 A1 | 7/2015 | Lyubomirskiy et al. |
| 2015/0181937 A1 | 7/2015 | Dubief et al. |
| 2015/0196058 A1 | 7/2015 | Lord |
| 2015/0201675 A1 | 7/2015 | Lord |
| 2015/0208728 A1 | 7/2015 | Lord |
| 2015/0250232 A1 | 9/2015 | Hon |
| 2015/0313275 A1 | 11/2015 | Anderson et al. |
| 2016/0021934 A1 | 1/2016 | Cadieux et al. |
| 2016/0073693 A1 | 3/2016 | Reevell |
| 2016/0101909 A1 | 4/2016 | Schennum et al. |
| 2016/0106154 A1 | 4/2016 | Lord |
| 2016/0106155 A1 | 4/2016 | Reevell |
| 2016/0120218 A1 | 5/2016 | Schennum et al. |
| 2016/0150825 A1 | 6/2016 | Mironov et al. |
| 2016/0278163 A1 | 9/2016 | Chen |
| 2016/0353804 A1 | 12/2016 | Lord |
| 2017/0006916 A1 | 1/2017 | Liu |
| 2017/0027225 A1 | 2/2017 | Buchberger et al. |
| 2017/0042245 A1 | 2/2017 | Buchberger et al. |
| 2017/0135401 A1 | 5/2017 | Dickens |
| 2017/0143038 A1 | 5/2017 | Dickens |
| 2017/0188629 A1 | 7/2017 | Dickens et al. |
| 2017/0188630 A1 | 7/2017 | Buchberger |
| 2017/0197043 A1 | 7/2017 | Buchberger |
| 2017/0197044 A1 | 7/2017 | Buchberger |
| 2017/0197046 A1 | 7/2017 | Buchberger |
| 2017/0215476 A1 | 8/2017 | Dickens et al. |
| 2017/0224014 A1 | 8/2017 | Fraser |
| 2017/0231284 A1 | 8/2017 | Newns |
| 2017/0251725 A1 | 9/2017 | Buchberger et al. |
| 2018/0192705 A1 | 7/2018 | Lord |
| 2018/0235284 A1 | 8/2018 | Lord |
| 2019/0254350 A1 | 8/2019 | Lord |
| 2019/0289920 A1 | 9/2019 | Lord |
| 2021/0146067 A1 | 5/2021 | Buchberger |
| 2021/0196919 A1* | 7/2021 | Potharaju ............ A61M 16/107 |

FOREIGN PATENT DOCUMENTS

| | | |
|---|---|---|
| AT | 507187 B1 | 3/2010 |
| AT | 507188 A4 | 3/2010 |
| AT | 508244 A4 | 12/2010 |
| AT | 510405 A4 | 4/2012 |
| AT | 510504 A1 | 4/2012 |
| AU | 6391373 A | 6/1975 |
| AU | 6393173 A | 6/1975 |
| AU | 2015341516 B2 | 12/2017 |
| AU | 2015341517 B2 | 1/2018 |
| AU | 2015255045 B2 | 3/2018 |
| AU | 2015359102 B2 | 6/2018 |
| AU | 2017256084 B2 | 9/2020 |
| BR | 6402132 U | 7/1986 |
| BR | 112017009252 A2 | 1/2018 |
| CA | 2309376 A1 | 11/2000 |
| CA | 2446102 A1 | 4/2004 |
| CA | 2824970 A1 | 8/2012 |
| CA | 2909967 A1 | 11/2014 |
| CH | 698603 B1 | 9/2009 |
| CL | 199400288 A1 | 8/1995 |
| CL | 199900377 | 3/1999 |
| CL | 2004000365 A1 | 2/2005 |
| CL | 2012000958 A1 | 1/2013 |
| CL | 2013002357 A1 | 11/2013 |
| CL | 2017001108 A1 | 1/2018 |
| CL | 2017001137 A1 | 1/2018 |
| CN | 86103434 A | 11/1986 |
| CN | 1039530 A | 2/1990 |
| CN | 2092880 U | 1/1992 |
| CN | 1102647 A | 5/1995 |
| CN | 2220168 Y | 2/1996 |
| CN | 1126425 A | 7/1996 |
| CN | 1205849 A | 1/1999 |
| CN | 1312730 A | 9/2001 |
| CN | 1329567 A | 1/2002 |
| CN | 1333657 A | 1/2002 |
| CN | 1337903 A | 2/2002 |
| CN | 2485265 Y | 4/2002 |
| CN | 1530041 A | 9/2004 |
| CN | 2660914 Y | 12/2004 |
| CN | 1607911 A | 4/2005 |
| CN | 1607950 A | 4/2005 |
| CN | 2719043 Y | 8/2005 |
| CN | 1694765 A | 11/2005 |
| CN | 1703279 A | 11/2005 |
| CN | 2754386 Y | 2/2006 |
| CN | 2777995 Y | 5/2006 |
| CN | 1286409 C | 11/2006 |
| CN | 2904674 Y | 5/2007 |
| CN | 200966824 Y | 10/2007 |
| CN | 101115901 A | 1/2008 |
| CN | 201023852 Y | 2/2008 |
| CN | 201067079 Y | 6/2008 |
| CN | 201079011 Y | 7/2008 |
| CN | 101437496 A | 5/2009 |
| CN | 201238609 Y | 5/2009 |
| CN | 201240612 Y | 5/2009 |
| CN | 101557728 A | 10/2009 |
| CN | 201375023 Y | 1/2010 |
| CN | 101648041 A | 2/2010 |
| CN | 201430913 Y | 3/2010 |
| CN | 101843368 A | 9/2010 |
| CN | 201592850 U | 9/2010 |
| CN | 101878958 A | 11/2010 |
| CN | 101925309 A | 12/2010 |
| CN | 201657770 U | 12/2010 |
| CN | 101951796 A | 1/2011 |
| CN | 102014677 A | 4/2011 |
| CN | 201830900 U | 5/2011 |
| CN | 201860753 U | 6/2011 |
| CN | 102264249 A | 11/2011 |
| CN | 102264420 A | 11/2011 |
| CN | 102326869 A | 1/2012 |

(56) References Cited

FOREIGN PATENT DOCUMENTS

| | | |
|---|---|---|
| CN | 202122096 U | 1/2012 |
| CN | 102389166 A | 3/2012 |
| CN | 202172846 U | 3/2012 |
| CN | 102655773 A | 9/2012 |
| CN | 102753047 A | 10/2012 |
| CN | 102883766 A | 1/2013 |
| CN | 202722498 U | 2/2013 |
| CN | 202750708 U | 2/2013 |
| CN | 103052380 A | 4/2013 |
| CN | 103338664 A | 10/2013 |
| CN | 103491958 A | 1/2014 |
| CN | 103960782 A | 8/2014 |
| CN | 203986095 U | 12/2014 |
| CN | 204048047 U | 12/2014 |
| CN | 104602553 A | 5/2015 |
| CN | 204317492 U | 5/2015 |
| CN | 104684422 A | 6/2015 |
| CN | 204598339 U | 8/2015 |
| CN | 104983079 A | 10/2015 |
| CN | 105310114 A | 2/2016 |
| CN | 105394816 A | 3/2016 |
| CN | 205106385 U | 3/2016 |
| CN | 106102863 A | 11/2016 |
| CN | 106998820 B | 10/2019 |
| DE | 594585 | 3/1934 |
| DE | 1950439 A1 | 4/1971 |
| DE | 2653133 A1 | 5/1978 |
| DE | 2940797 A1 | 4/1981 |
| DE | 3148335 A1 | 7/1983 |
| DE | 3218760 A1 | 12/1983 |
| DE | 3936687 A1 | 5/1990 |
| DE | 29719509 U1 | 1/1998 |
| DE | 19630619 A1 | 2/1998 |
| DE | 19654945 A1 | 3/1998 |
| DE | 29803260 U1 | 7/1998 |
| DE | 10330681 B3 | 6/2004 |
| DE | 202006013439 U1 | 10/2006 |
| DE | 102006004484 A1 | 8/2007 |
| DE | 202013100606 U1 | 2/2013 |
| EA | 009116 B1 | 10/2007 |
| EA | 019736 B1 | 5/2014 |
| EA | 022685 B1 | 2/2016 |
| EA | 201692191 A1 | 3/2017 |
| EP | 0280262 A2 | 8/1988 |
| EP | 0283672 A2 | 9/1988 |
| EP | 0289342 A2 | 11/1988 |
| EP | 0290911 A2 | 11/1988 |
| EP | 0295122 A2 | 12/1988 |
| EP | 0358002 A2 | 3/1990 |
| EP | 0358114 A2 | 3/1990 |
| EP | 0444553 A2 | 9/1991 |
| EP | 0488488 A1 | 6/1992 |
| EP | 0520231 A2 | 12/1992 |
| EP | 0845220 A1 | 6/1998 |
| EP | 0847220 A2 | 6/1998 |
| EP | 0893071 A1 | 1/1999 |
| EP | 0893171 A1 | 1/1999 |
| EP | 1166814 A2 | 1/2002 |
| EP | 1166847 A2 | 1/2002 |
| EP | 1468618 A1 | 10/2004 |
| EP | 1509227 A1 | 3/2005 |
| EP | 1618803 A1 | 1/2006 |
| EP | 1736065 A1 | 12/2006 |
| EP | 1757921 A2 | 2/2007 |
| EP | 1772166 A1 | 4/2007 |
| EP | 1772199 A1 | 4/2007 |
| EP | 1820748 A1 | 8/2007 |
| EP | 1847671 A1 | 10/2007 |
| EP | 1950439 A1 | 7/2008 |
| EP | 2018886 A1 | 1/2009 |
| EP | 2022349 A1 | 2/2009 |
| EP | 2022350 A1 | 2/2009 |
| EP | 1509227 B1 | 10/2009 |
| EP | 2113178 A1 | 11/2009 |
| EP | 2234891 A2 | 10/2010 |
| EP | 2340729 A1 | 7/2011 |
| EP | 2358223 A1 | 8/2011 |
| EP | 2358418 A1 | 8/2011 |
| EP | 2404515 A1 | 1/2012 |
| EP | 2468116 A1 | 6/2012 |
| EP | 2468118 A1 | 6/2012 |
| EP | 2477607 A1 | 7/2012 |
| EP | 2698070 A1 | 2/2014 |
| EP | 2762019 A1 | 8/2014 |
| EP | 2779786 A1 | 9/2014 |
| EP | 2785208 A1 | 10/2014 |
| EP | 2801273 A2 | 11/2014 |
| EP | 2835062 A1 | 2/2015 |
| EP | 2871985 A1 | 5/2015 |
| EP | 2907397 A1 | 8/2015 |
| EP | 2967144 A1 | 1/2016 |
| EP | 2993999 A1 | 3/2016 |
| EP | 3021699 A2 | 5/2016 |
| EP | 3073846 A2 | 10/2016 |
| EP | 3076805 A1 | 10/2016 |
| EP | 3145348 A1 | 3/2017 |
| EP | 2907397 B1 | 9/2017 |
| EP | 3284500 A1 | 2/2018 |
| EP | 3117860 B1 | 1/2019 |
| EP | 3214957 B1 | 2/2019 |
| EP | 3229621 B1 | 1/2020 |
| EP | 3491941 B1 | 8/2020 |
| EP | 3738632 B1 | 2/2022 |
| FR | 472030 A | 11/1914 |
| FR | 960469 A | 4/1950 |
| FR | 1292446 A | 5/1962 |
| GB | 190903566 A | 6/1909 |
| GB | 190930472 | 12/1909 |
| GB | 191100628 A | 11/1911 |
| GB | 25575 A | 3/1912 |
| GB | 191311086 A | 9/1913 |
| GB | 110216 A | 10/1917 |
| GB | 111454 A | 11/1917 |
| GB | 120016 A | 10/1918 |
| GB | 160493 A | 3/1921 |
| GB | 163124 A | 5/1921 |
| GB | 215992 A | 5/1924 |
| GB | 220229 A | 8/1924 |
| GB | 268967 A | 4/1927 |
| GB | 402064 A | 11/1933 |
| GB | 438750 A | 11/1935 |
| GB | 507955 A | 6/1939 |
| GB | 544329 A | 4/1942 |
| GB | 565574 A | 11/1944 |
| GB | 611596 A | 11/1948 |
| GB | 626888 A | 7/1949 |
| GB | 871869 A | 7/1961 |
| GB | 1313525 A | 4/1973 |
| GB | 2133691 A | 8/1984 |
| GB | 1046183 | 7/1988 |
| GB | 2275464 A | 8/1994 |
| GB | 2068034 | 11/1997 |
| GB | 2369108 A | 5/2002 |
| GB | 4000273 | 12/2006 |
| GB | 4006615 | 10/2008 |
| GB | 2504075 A | 1/2014 |
| GB | 2513635 A | 11/2014 |
| HK | 1196511 A1 | 12/2014 |
| HK | 1226611 | 10/2017 |
| IE | S20060065 A2 | 10/2006 |
| IN | 0351/KOL/2006 | 7/2007 |
| JP | S5289386 A | 7/1977 |
| JP | S5752456 A | 3/1982 |
| JP | S57140354 A | 8/1982 |
| JP | S59106340 A | 6/1984 |
| JP | S59135878 A | 8/1984 |
| JP | S6121542 A | 1/1986 |
| JP | S6121542 B2 | 5/1986 |
| JP | S6196763 A | 5/1986 |
| JP | S6196765 A | 5/1986 |
| JP | H01104153 A | 4/1989 |
| JP | H01117775 A | 5/1989 |
| JP | H02124081 A | 5/1990 |
| JP | H02124082 A | 5/1990 |

(56) References Cited

FOREIGN PATENT DOCUMENTS

| | | |
|---|---|---|
| JP | H0548944 A | 2/1993 |
| JP | H05103836 A | 4/1993 |
| JP | H05309136 A | 11/1993 |
| JP | 3003543 U | 10/1994 |
| JP | H06303837 A | 11/1994 |
| JP | H06315366 A | 11/1994 |
| JP | H07147965 A | 6/1995 |
| JP | H08299862 A | 11/1996 |
| JP | H08511176 A | 11/1996 |
| JP | H1189551 A | 4/1999 |
| JP | H11503912 A | 4/1999 |
| JP | H11514018 A | 11/1999 |
| JP | H11514081 A | 11/1999 |
| JP | 3003543 B2 | 1/2000 |
| JP | 2001502542 A | 2/2001 |
| JP | 2001248842 A | 9/2001 |
| JP | 2002527153 A | 8/2002 |
| JP | 2003024036 A | 1/2003 |
| JP | 3093201 U | 4/2003 |
| JP | 2003226577 A | 8/2003 |
| JP | 2004097617 A | 4/2004 |
| JP | 2004512907 A | 4/2004 |
| JP | 2004332069 A | 11/2004 |
| JP | 2005013092 A | 1/2005 |
| JP | 2005034021 A | 2/2005 |
| JP | 2005514991 A | 5/2005 |
| JP | 2005138773 A | 6/2005 |
| JP | 2005524067 A | 8/2005 |
| JP | 2005533770 A | 11/2005 |
| JP | 2005537918 A | 12/2005 |
| JP | 2005537919 A | 12/2005 |
| JP | 2005538149 A | 12/2005 |
| JP | 2005538159 A | 12/2005 |
| JP | 2006305336 A | 11/2006 |
| JP | 2007057532 A | 3/2007 |
| JP | 2007097787 A | 4/2007 |
| JP | 2007512880 A | 5/2007 |
| JP | 2007297124 A | 11/2007 |
| JP | 2008501406 A | 1/2008 |
| JP | 2008544834 A | 12/2008 |
| JP | 2009509523 A | 3/2009 |
| JP | 2009526714 A | 7/2009 |
| JP | 2009529871 A | 8/2009 |
| JP | 2009537119 A | 10/2009 |
| JP | 2010080261 A | 4/2010 |
| JP | 2011087569 A | 5/2011 |
| JP | 2011515093 A | 5/2011 |
| JP | 2011518567 A | 6/2011 |
| JP | 2012013247 A | 1/2012 |
| JP | 2012026933 A | 2/2012 |
| JP | 2012029633 A | 2/2012 |
| JP | 2012057859 A | 3/2012 |
| JP | 2012506263 A | 3/2012 |
| JP | 2012223190 A | 11/2012 |
| JP | 2012249854 A | 12/2012 |
| JP | 2013516159 A | 5/2013 |
| JP | 2013521075 A | 6/2013 |
| JP | 2013545473 A | 12/2013 |
| JP | 2014501107 A | 1/2014 |
| JP | 2014511175 A | 5/2014 |
| JP | 2014516624 A | 7/2014 |
| JP | 2014520542 A | 8/2014 |
| JP | 2014524313 A | 9/2014 |
| JP | 2014525251 A | 9/2014 |
| JP | 2015500025 A | 1/2015 |
| JP | 2015505476 A | 2/2015 |
| JP | 2015506182 A | 3/2015 |
| JP | 2015513970 A | 5/2015 |
| JP | 2015521847 A | 8/2015 |
| JP | 2016510994 A | 4/2016 |
| JP | 2016520061 A | 7/2016 |
| JP | 2017518033 A | 7/2017 |
| JP | 2017522868 A | 8/2017 |
| JP | 2017525348 A | 9/2017 |
| JP | 6507248 B2 | 4/2019 |
| KR | 920017172 A | 9/1992 |
| KR | 100244670 B1 | 2/2000 |
| KR | 20050037919 A | 4/2005 |
| KR | 20090008142 U | 8/2009 |
| KR | 20100006995 U | 7/2010 |
| KR | 20110006928 U | 7/2011 |
| KR | 20120025569 A | 3/2012 |
| KR | 20120070731 A | 7/2012 |
| KR | 20120104183 A | 9/2012 |
| KR | 20130004985 A | 1/2013 |
| KR | 20130006714 A | 1/2013 |
| KR | 20130006714 U | 11/2013 |
| KR | 200470732 Y1 | 1/2014 |
| KR | 20140128449 A | 11/2014 |
| KR | 101955000 B1 | 3/2019 |
| KR | 102148901 B1 | 8/2020 |
| NL | 6617184 A | 6/1967 |
| PH | 12017500957 B1 | 10/2017 |
| RU | 2311859 C2 | 12/2007 |
| RU | 2328192 C1 | 7/2008 |
| RU | 2330314 C2 | 7/2008 |
| RU | 2333014 C2 | 9/2008 |
| RU | 2336001 C2 | 10/2008 |
| RU | 2360583 C1 | 7/2009 |
| RU | 89927 U1 | 12/2009 |
| RU | 94815 U1 | 6/2010 |
| RU | 103281 U1 | 4/2011 |
| RU | 115629 U1 | 5/2012 |
| RU | 121706 U1 | 11/2012 |
| RU | 122000 U1 | 11/2012 |
| RU | 124120 U1 | 1/2013 |
| RU | 2476331 C1 | 2/2013 |
| RU | 132318 U1 | 9/2013 |
| RU | 2509516 C2 | 3/2014 |
| UA | 88052 C2 | 9/2009 |
| UA | 89752 C2 | 3/2010 |
| UA | 67598 U | 2/2012 |
| UA | 78167 U | 3/2013 |
| WO | 9503050 A2 | 2/1995 |
| WO | WO-9527412 A1 | 10/1995 |
| WO | WO-9632854 A2 | 10/1996 |
| WO | WO-9748293 A1 | 12/1997 |
| WO | WO-9817131 A1 | 4/1998 |
| WO | WO-0009188 A1 | 2/2000 |
| WO | WO-0021598 A1 | 4/2000 |
| WO | WO-0028842 A1 | 5/2000 |
| WO | WO-0050111 A1 | 8/2000 |
| WO | 0102040 A1 | 1/2001 |
| WO | 0122907 A1 | 4/2001 |
| WO | WO-02051468 A2 | 7/2002 |
| WO | WO-02058747 A1 | 8/2002 |
| WO | WO-02060769 A1 | 8/2002 |
| WO | WO-03005045 A1 | 1/2003 |
| WO | WO-03028409 A1 | 4/2003 |
| WO | WO-03050405 A1 | 6/2003 |
| WO | 03055486 A1 | 7/2003 |
| WO | 03059424 A1 | 7/2003 |
| WO | WO-03083283 A1 | 10/2003 |
| WO | WO-03101454 A1 | 12/2003 |
| WO | WO-2004022128 A2 | 3/2004 |
| WO | WO-2004022242 A1 | 3/2004 |
| WO | WO-2004022243 A1 | 3/2004 |
| WO | 2004029050 A1 | 4/2004 |
| WO | 2004065348 A1 | 8/2004 |
| WO | 2004076289 A2 | 9/2004 |
| WO | 2004076412 A2 | 9/2004 |
| WO | 2004076289 A3 | 12/2004 |
| WO | 2005004989 A2 | 1/2005 |
| WO | 2005039531 A1 | 5/2005 |
| WO | 2005075452 A1 | 8/2005 |
| WO | 2005089728 A2 | 9/2005 |
| WO | 2005108389 A1 | 11/2005 |
| WO | WO-2005106350 A2 | 11/2005 |
| WO | 2005120614 A1 | 12/2005 |
| WO | 2006004646 A1 | 1/2006 |
| WO | 2006008108 A2 | 1/2006 |
| WO | 2006034833 A1 | 4/2006 |
| WO | 2006073366 A1 | 7/2006 |
| WO | WO-2006082571 A1 | 8/2006 |

(56) References Cited

FOREIGN PATENT DOCUMENTS

| | | |
|---|---|---|
| WO | 2007002597 A2 | 1/2007 |
| WO | 2007038215 A1 | 4/2007 |
| WO | WO-2007040941 A1 | 4/2007 |
| WO | WO-2007042941 A2 | 4/2007 |
| WO | WO-2007108877 A2 | 9/2007 |
| WO | WO-2007131448 A1 | 11/2007 |
| WO | WO-2007131449 A1 | 11/2007 |
| WO | WO-2007141668 A2 | 12/2007 |
| WO | WO-2008006048 A2 | 1/2008 |
| WO | 2008015918 A1 | 2/2008 |
| WO | WO-2008038144 A2 | 4/2008 |
| WO | 2008073942 A2 | 6/2008 |
| WO | WO-2008104870 A1 | 9/2008 |
| WO | WO-2009001085 A2 | 12/2008 |
| WO | 2009007767 A1 | 1/2009 |
| WO | 2009007768 A1 | 1/2009 |
| WO | 2009007769 A1 | 1/2009 |
| WO | 2009007770 A1 | 1/2009 |
| WO | 2009007771 A1 | 1/2009 |
| WO | WO-2009015410 A1 | 2/2009 |
| WO | 2009079641 A2 | 6/2009 |
| WO | WO2009092419 A2 | 7/2009 |
| WO | WO-2009092862 A1 | 7/2009 |
| WO | WO-2009092419 A3 | 9/2009 |
| WO | WO-2009118085 A1 | 10/2009 |
| WO | 2009135729 A1 | 11/2009 |
| WO | WO-2009132793 A1 | 11/2009 |
| WO | WO-2010045670 A1 | 4/2010 |
| WO | WO-2010045671 A1 | 4/2010 |
| WO | 2011034723 A1 | 3/2011 |
| WO | 2011045609 A1 | 4/2011 |
| WO | WO-2011050943 A1 | 5/2011 |
| WO | WO-2011050964 A1 | 5/2011 |
| WO | WO-2011079932 A1 | 7/2011 |
| WO | WO-2011109849 A1 | 9/2011 |
| WO | 2011139684 A2 | 11/2011 |
| WO | 2011139811 A1 | 11/2011 |
| WO | WO-2011137453 A2 | 11/2011 |
| WO | WO-2012025496 A1 | 3/2012 |
| WO | WO-2012065310 A1 | 5/2012 |
| WO | WO-2012065754 A2 | 5/2012 |
| WO | WO-2012085203 A1 | 6/2012 |
| WO | WO-2012085207 A1 | 6/2012 |
| WO | 2012110819 A1 | 8/2012 |
| WO | WO-2012106739 A1 | 8/2012 |
| WO | WO-2012114082 A1 | 8/2012 |
| WO | 2012134380 A1 | 10/2012 |
| WO | 2012142293 A2 | 10/2012 |
| WO | WO-2013013808 A1 | 1/2013 |
| WO | WO-2013025921 A1 | 2/2013 |
| WO | 2013034452 A1 | 3/2013 |
| WO | WO-2013034453 A1 | 3/2013 |
| WO | WO-2013034460 A1 | 3/2013 |
| WO | WO-2013045942 A2 | 4/2013 |
| WO | WO-2013057185 A1 | 4/2013 |
| WO | WO-2013082173 A1 | 6/2013 |
| WO | WO-2013083631 A1 | 6/2013 |
| WO | WO-2013098395 A1 | 7/2013 |
| WO | 2013110210 A1 | 8/2013 |
| WO | 2013116561 A1 | 8/2013 |
| WO | WO-2013116558 A1 | 8/2013 |
| WO | WO-2013116571 A1 | 8/2013 |
| WO | WO-2013116572 A1 | 8/2013 |
| WO | WO-2013142671 A1 | 9/2013 |
| WO | WO-2013152873 A1 | 10/2013 |
| WO | WO-2013178769 A1 | 12/2013 |
| WO | WO-2013189050 A1 | 12/2013 |
| WO | WO-2013189052 A1 | 12/2013 |
| WO | 2014004648 A1 | 1/2014 |
| WO | WO-2014005275 A1 | 1/2014 |
| WO | WO-2014012906 A1 | 1/2014 |
| WO | WO2014012907 A1 | 1/2014 |
| WO | WO-2014015463 A1 | 1/2014 |
| WO | WO-2014061477 A1 | 4/2014 |
| WO | WO-2014071329 A1 | 5/2014 |
| WO | WO-2014130695 A1 | 8/2014 |
| WO | 2014150245 A1 | 9/2014 |
| WO | 2014151434 A2 | 9/2014 |
| WO | WO-2014140320 A1 | 9/2014 |
| WO | WO-2014150131 A1 | 9/2014 |
| WO | 2014159240 A1 | 10/2014 |
| WO | 2014159250 A1 | 10/2014 |
| WO | 2014177859 A1 | 11/2014 |
| WO | 2014182736 A1 | 11/2014 |
| WO | 2014190079 A2 | 11/2014 |
| WO | 2015009862 A2 | 1/2015 |
| WO | 2015054885 A1 | 4/2015 |
| WO | 2015084544 A1 | 6/2015 |
| WO | 2015091258 A1 | 6/2015 |
| WO | WO-2015114327 A1 | 8/2015 |
| WO | WO-2015114328 A1 | 8/2015 |
| WO | 2015149404 A1 | 10/2015 |
| WO | 2015167629 A1 | 11/2015 |
| WO | 2015179292 A1 | 11/2015 |
| WO | WO-2015165812 A1 | 11/2015 |
| WO | 2015189623 A1 | 12/2015 |
| WO | 2015198049 A1 | 12/2015 |
| WO | 2016071705 A1 | 5/2016 |
| WO | 2016071706 A1 | 5/2016 |

OTHER PUBLICATIONS

Application and File History for U.S. Appl. No. 13/125,343, filed Apr. 21, 2011, inventor Buchberger.
Application and File History for U.S. Appl. No. 13/984,512, filed Aug. 29, 2013, inventor Buchberger.
Application and File History for U.S. Appl. No. 14/235,210, filed Mar. 4, 2014, inventor Buchberger, 504 pages.
Application and File History for U.S. Appl. No. 14/268,909, filed May 2, 2014, inventor Buchberger.
Application and File History for U.S. Appl. No. 14/296,803, filed Jun. 5, 2014, inventor Buchberger, 627 pages.
Application and File History for U.S. Appl. No. 14/306,831, filed Jun. 17, 2014, inventor Buchberger.
Application and File History for U.S. Appl. No. 14/353,256, filed Apr. 21, 2014, inventor Buchberger, 375 pages.
Application and File History for U.S. Appl. No. 14/594,065, filed Jan. 9, 2015, Inventor Buchberger, 302 pages.
Application and File History for U.S. Appl. No. 14/787,946, filed Oct. 29, 2015, inventor Lord, 228 pages.
Application and File History for U.S. Appl. No. 14/888,514, filed Nov. 2, 2015, inventor Reevell, 188 pages.
Application and File History for U.S. Appl. No. 14/888,517, filed Nov. 2, 2015, Inventor Reevell, 136 pages.
Application and File History for U.S. Appl. No. 15/307,095, filed Oct. 27, 2016, inventor Buchberger, 288 pages.
Application and File History for U.S. Appl. No. 15/454,156, filed Mar. 9, 2017, inventor Buchberger, 61 pages.
Application and File History for U.S. Appl. No. 15/470,078, filed Mar. 27, 2017, inventor Buchberger, 392 pages.
Application and File History for U.S. Appl. No. 15/470,089, filed Mar. 27, 2017, inventor Buchberger, 558 pages.
Application and File History for U.S. Appl. No. 15/470,095, filed Mar. 27, 2017, inventor Buchberger, 351 pages.
Application and File History for U.S. Appl. No. 15/997,113, filed Jun. 4, 2018, inventor Buchberger.
Application and File History for U.S. Appl. No. 16/096,554, filed Oct. 25, 2018, Inventor Fraser.
Company Filtrona Richmond Inc., www.filtronaporoustechnologies.com, Nov. 19, 2018, 1 page.
Decision on Appeal, U.S. Appl. No. 14/306,831, mailing date Mar. 26, 2020, 6 pages.
Decision to Grant a Patent dated May 22, 2018 for Japanese Application No. 2016-134648, 5 pages.
Decision to Grant dated Feb. 5, 2018 for Ukraine Application No. 201607243, 6 pages.
Decision to Grant dated Apr. 11, 2016 for Russian Application No. 2015100321, 8 pages (No translation available).

(56) References Cited

OTHER PUBLICATIONS

Decision to Grant dated Jun. 23, 2016 for Ukrainian Application No. 201500198, 6 pages (No translation available).
Decision to Grant dated Apr. 27, 2017 for Russian Application No. 2015146845, 8 pages.
Decision to Grant for Australian Application No. 2017105898, dated Mar. 16, 2018, 12 pages.
Decision to Grant for Great Britain Application No. GB1405720.2, dated Sep. 26, 2017, 2 pages.
Decision to Grant for Russian Application No. 120267, dated Oct. 26, 2016, 7 pages.
Decision to Grant dated Apr. 1, 2014 for Russian Application No. 2011120430, 16 pages.
Decision to Grant dated Aug. 5, 2014 for Japanese Application No. 2011-532464, 6 pages.
Diener Electronic, "Plasma Polymerization," The company Diener electronic GmbH+Co. KG, Retrieved on Oct. 17, 2017, 19 pages.
Dunn P.D., et al., "Heat Pipes," Fourth Edition, Pergamon, ISBN0080419038, 1994, 14 pages.
ECF, "Welcome to the World's Largest E-Cigarette Website: The Voice of Vaping since 2007," Oct. 2011, Nichrome or Kanthal Specs for Purchasing, retrieved on Apr. 19, 2020, 6 pages.
Examination Report for Great Britain Application No. GB1405720. 2, dated Jun. 27, 2017, 3 pages.
Examination Report dated Nov. 20 for Australian Application No. 2017256084, 3 pages.
Examination Report dated Dec. 15, 2017, for Australian Application No. 201512626, 3 pages.
Extended European Search Report for Application No. 15178588, dated Apr. 14, 2016, 2 pages.
Extended European Search Report for Application No. 16166656, dated Oct. 11, 2016, 9 pages.
Extended European Search Report for Application No. 17189951.1, dated Jan. 4, 2018, 11 pages.
Extended European Search Report for Application No. 18205608.5, dated Jul. 12, 2019, 7 pages.
Extended European Search Report for Application No. EP17197150. 5, dated Mar. 1, 2018, 6 pages.
Extended European Search Report for Application No. 16151458.3, dated Jul. 11, 2016, 8 pages.
Extended European Search Report for Application No. 19196432.9, dated Dec. 9, 2019, 14 pages.
Extended European Search Report for European Application No. 15178588, dated Apr. 22, 2016, 4 pages.
First Office Action for Chinese Application No. 201480031926.5 dated Apr. 21, 2017, 12 pages.
First Office Action dated Dec. 3, 2012 for Chinese Application No. 200980152395.4, 16 pages.
Hegbom T., "Integrating Electrical Heating Elements in Appliance Design," resulting in interlocutory decision dated Aug. 7, 2019, 4 pages.
Hong Kong Publication, Application No. 14110165.2, published on Dec. 19, 2014, 1 page.
Hong Kong Publication, Application No. 16113324.2, published on Oct. 6, 2017, 1 page.
Iatty, "An Idea of the Iatty, Welcome to the World's Largest E-Cigarette Website: The Voice of Vaping since 2007," retrieved on Dec. 17, 2019, p. 23, Post 443 and 445, 7 pages.
Iatty, "An Idea of the Iatty, Welcome to the World's Largest E-Cigarette Website: The Voice of Vaping since 2007," retrieved on Dec. 17, 2019, p. 24, Post 467, 6 pages.
Iatty, "An Idea of the Iatty, Welcome to the World's Largest E-Cigarette Website: The Voice of Vaping since 2007," retrieved on Dec. 17, 2019, p. 37, Post 727, 6 pages.
Iatty, "An Idea of the Iatty, Welcome to the World's Largest E-Cigarette Website: The Voice of Vaping since 2007," retrieved on Dec. 17, 2019, Page, Post 1, 7 pages.
"Integrating Electrical Heating Elements in Product Design," Metallic Resistance Heating Wire, Chapter 1, Section 1.1 to 1.3.2, resulting in interlocutory decision dated Aug. 7, 2019, 6 pages.
"Integrating Electrical Heating Elements in Product Design," Metallic Resistance Heating Wire, Chapter 1, Section 1.4, resulting in interlocutory decision dated Aug. 7, 2019, 1 page.
"Integrating Electrical Heating Elements in Product Design," Metallic Resistance Heating Wire, resulting in interlocutory decision dated Aug. 7, 2019, 8 pages.
International Preliminary Report on Patentability for Application No. PCT/AT2009/000413, dated May 5, 2011, 7 pages.
International Preliminary Report on Patentability for Application No. PCT/AT2009/000414, dated Apr. 26, 2011, 7 pages.
International Preliminary Report on Patentability for Application No. PCT/AT2012/000017, dated Aug. 13, 2013, 5 pages.
International Preliminary Report on Patentability for Application No. PCT/EP2012/003103, dated Feb. 6, 2014, 7 pages.
International Preliminary Report on Patentability for Application No. PCT/EP2012/070647, dated Apr. 22, 2014, 8 pages.
International Preliminary Report on Patentability for Application No. PCT/GB2014/051332, dated Nov. 12, 2015, 7 pages.
International Preliminary Report on Patentability for Application No. PCT/GB2014/051333, dated Aug. 5, 2015, 12 pages.
International Preliminary Report on Patentability for Application No. PCT/GB2014/051334, dated Nov. 12, 2015, 7 pages.
International Preliminary Report on Patentability for Application No. PCT/GB2014/051688, dated Dec. 17, 2015, 6 pages.
International Preliminary Report on Patentability for Application No. PCT/GB2015/050195, dated May 13, 2016, 17 pages.
International Preliminary Report on Patentability for Application No. PCT/GB2015/051213, dated Jul. 14, 2016, 20 pages.
International Preliminary Report on Patentability for Application No. PCT/GB2015/053445, dated Jan. 24, 2017, 19 pages.
International Preliminary Report on Patentability for Application No. PCT/GB2017/051139, dated Aug. 6, 2018, 7 pages.
International Preliminary Report on Patentability dated Sep. 9, 2014 for Application No. PCT/EP2013/64922, filed Jul. 15, 2013, 10 pages.
International Search Report and Written Opinion for Application No. PCT/AT2012/000017, dated Jul. 3, 2012, 6 pages.
International Search Report and Written Opinion for Application No. PCT/EP2012/003103, dated Nov. 26, 2012, 6 pages.
International Search Report and Written Opinion for Application No. PCT/EP2012/070647, dated Feb. 6, 2013, 9 pages.
International Search Report and Written Opinion for Application No. PCT/GB2014/051332, dated Jul. 21, 2014, 8 pages.
International Search Report and Written Opinion for Application No. PCT/GB2014/051333, dated Jul. 17, 2014, 10 pages.
International Search Report and Written Opinion for Application No. PCT/GB2014/051334, dated Jul. 21, 2014, 8 pages.
International Search Report and Written Opinion for Application No. PCT/GB2015/053445, dated Apr. 18, 2016, 21 pages.
International Search Report and Written Opinion for Application No. PCT/GB2017/051139, dated Aug. 9, 2017, 14 pages.
International Search Report and Written Opinion dated Oct. 11, 2013 for Application No. PCT/EP2013/064922, filed Jul. 15, 2013, 6 pages.
International Search Report for App No. PCT/GB2015/050195, dated Sep. 2, 2015, 4 pages.
International Search Report for Application No. PCT/AT2009/000413, dated Jan. 25, 2010, 3 pages.
International Search Report for Application No. PCT/AT2009/000414, dated Jan. 26, 2010, 2 pages.
International Search Report for Application No. PCT/GB2014/051633, dated Dec. 4, 2014, 7 pages.
International Search Report for Application No. PCT/GB2014/051688, dated Aug. 26, 2014, 4 pages.
International Search Report for Application No. PCT/GB2015/051213, dated Jul. 16, 2015, 5 pages.
Kynol, "Standard Specifications of Kynol™ Activated Carbon Fiber Products," Sep. 19, 2013, 2 pages.
Iatty, "E-Cigarette Forum," p. 10, May 2011, commentary by Imeothanasis and Iorderos33, retrieved on Feb. 11, 2019, 8 pages.
Notice of Allowance dated Oct. 18, 2019 for Korean Application No. 1020167018457, 2 pages (with translation—3 pages).

(56) References Cited

OTHER PUBLICATIONS

Notice of Allowance dated May 30, 2017 for Korean Application No. 1020157001277, 4 pages (No translation available).
Notice of Allowance dated Jun. 27, 2018 for Korean Application No. 1020167020977, 3 pages.
Notice of Opposition Letter from EPO Opposition against the European Application No. 2358418, mailed Mar. 1, 2017, 60 pages.
Notice of Opposition mailed Oct. 30, 2019 for European Application No. 16166656.5, 39 pages.
Notice of Reasons for Rejection for Japanese Application No. 2020-121265, dated Jul. 20, 2021, 8 pages.
Notice of Reasons for Rejection dated Oct. 15, 2013 for Japanese Application No. 2011532464, 6 pages.
Notice of Reasons for Rejection dated May 23, 2017 for Japanese Application No. 2016134648, 18 pages.
Notice of Reasons for Rejection dated May 31, 2016 for Japanese Application No. 2015-137361, 6 pages.
Notice of Reasons for Rejection dated Oct. 7, 2013 for Japanese Application No. 2011532464, 6 pages.
Notice of Reasons for Rejection dated Sep. 8, 2015 for Japanese Application No. 2014179732, 5 pages.
Notice of Reasons for Revocation dated Apr. 17, 2017 for Japanese Patent No. 5960358, with English translation, 12 pages.
Notification of Transmittal of IPRP for International Application No. PCT/GB2014/051633 dated Oct. 23, 2015, 9 pages.
Notification to Grant Patent Right for Invention dated Oct. 25, 2018 for Chinese Application No. 201610086101.4, 2 pages.
Office Action and Search Report dated Feb. 28, 2019 for Japanese Application No. 2018-088088, 25 pages.
Office Action dated Sep. 3, 2014, for Russian Application No. 2013504605, 7 pages.
Office Action dated Jul. 2, 2020 for Chinese Application No. 201780020023.0 filed Sep. 25, 2018, 22 pages.
Office Action dated Nov. 21, 2017 for Russian Application No. 2016142584, 8 pages.
Office Action dated Nov. 22, 2016 for Canadian Application No. 2878951, 3 pages.
Office Action dated Sep. 22, 2017 for Russian Application No. 2015146847, 11 pages.
Office Action dated Nov. 23, 2018 for Korean Application No. 1020167018457, 6 pages (12 pages with translation).
Office Action dated Apr. 25, 2017 for Japanese Application No. 2016123816, 2 pages (No translation available).
Office Action dated May 12, 2017 for Korean Application No. 10-20157034538, 10 pages.
Office Action for European Application No. 16166656, dated Jul. 29, 2020, 7 pages.
Office Action for Chilean Application No. 201701486 dated Nov. 11, 2019, 10 pages.
Office Action for Chinese Application No. 201480031296.1 dated Mar. 27, 2017, 13 pages.
Office Action For Chinese Application No. 201780020023.0, dated Mar. 8, 2021, 19 pages.
Office Action dated Jun. 2, 2016 for Chinese Application No. 201380038075.2, 7 pages (with translation—19 pages).
Office Action dated Sep. 11, 2017 for Chinese Application No. 201480024988.3, 10 pages.
Office Action dated Dec. 12, 2018 for Korean Application No. 10-2017-7015164, 3 pages.
Office Action dated Jun. 15, 2018 for Korean Application No. 10-2017-7015164, 13 pages.
Office Action dated Mar. 16, 2020 for Chinese Patent Application No. 201610255788.X, filed Oct. 21, 2009, 21 pages.
Office Action dated Jan. 18, 2017 for Chinese Application No. 201480024978.X, 8 pages.
Office Action dated Jul. 18, 2018 for Chinese Application No. 201580022356.8, 15 pages.
Office Action dated Sep. 22, 2017 for Russian Application No. 2014120213, 11 pages.
Office Action dated Jan. 25, 2019 for European Application No. 17189951.1, 4 pages.
Office Action dated Jun. 26, 2018 for Japanese Application No. 2017-530762, 16 pages.
Office Action dated Nov. 26, 2019 for Brazilian Application No. 112015000872, 4 pages.
Office Action dated Oct. 26, 2016 for Russian Application No. 2014120213, 7 pages.
Office Action dated Sep. 27, 2019 for Korean Application No. 10-20197005785, 13 pages.
Office Action dated Dec. 30, 2016 for Chinese Application No. 201480024988.3, 26 pages.
Office Action dated Sep. 30, 2018 for Chinese Application No. 201610371843.1, 8 pages.
Office Action dated May 4, 2018 for Chinese Application No. 201610086101.4, 7 pages.
Office Action dated Dec. 5, 2017 for Japanese Application No. 2016-564977, 6 pages.
Office Action dated Apr. 10, 2019, for Korean Application No. 1020167018457, 13 pages.
Office Action dated Apr. 23, 2018 for Chinese Application No. 201580006377.0, 9 pages (20 pages with translation).
Office Action dated Dec. 8, 2017, for Korean Application No. 1020167020977, 13 pages.
Office Action dated Jan. 23, 2018, for Japanese Application No. 2016548373, 3 pages, (6 pages with translation).
Office Action dated Jun. 5, 2018, for Chinese Application No. 201610552323.0, 11 pages, (18 pages with translation).
Office Action dated Mar. 14, 2018, for Russian Application No. 2016131333, 7 pages (13 pages with translation).
Opposition Statement dated Mar. 30, 2017 for Japanese Patent No. 5960358, 144 pages (No translation available).
Partial EPO Opposition, resulting in interlocutory decision dated Aug. 7, 2019, 75 pages.
Rudolph G., "The Influence of CO2 on the Sensory Characteristics of the Favor-System," 1987, Accessed at http://legacy.library.ucsf.edu/tid/sld5f100, 24 pages.
Search Report for Chilean Application No. 2019-11665, dated Nov. 11, 2019, 10 pages.
Search Report for Japanese Application No. 2011532464, dated Sep. 18, 2013, 116 pages.
Search Report for Japanese Application No. 2014-179732, dated Sep. 9, 2015, 12 pages.
Search Report for Japanese Application No. 2016134648, dated Mar. 28, 2017, 29 pages.
Search Report for Japanese Application No. 2016-564977, dated Oct. 25, 2017, 19 pages.
Search Report for Japanese Application No. 2011532464, dated Sep. 24, 2013, 53 pages.
Search Report dated Feb. 1, 2017 for Japanese Application No. 2016517671, 13 pages.
Search Report dated Apr. 14, 2017 for Japanese Application No. 2016-134648, 31 pages.
Search Report dated Sep. 19, 2013 for Japanese Application No. 2011-532464, 116 pages.
Search Report dated Apr. 24, 2017 for Russian Application No. 2015146843, 3 pages.
Search Report dated Jun. 24, 2019 for Russian Application No. 2018137583, 2 pages.
Search Report dated Apr. 25, 2018 for Chinese Application No. 201610086101.4, 1 page.
Search Report dated Aug. 25, 2015 for Japanese Application No. 2014-179732, 10 pages.
Search Report dated Oct. 25, 2017 for Japanese Application No. 2016-864977, 19 pages.
Search Report dated Apr. 29, 2019 for Russian Application No. 2018137501, 12 pages.
Search Report dated May 29, 2015 for Great Britain Application No. 1422018, 3 pages.
Search Report dated Mar. 20, 2015, for Great Britain Application No. GB1401520.0, 2 pages.
Second Office Action dated Aug. 20, 2013 for Chinese Application No. 200980152395.4, 16 pages.

(56) References Cited

OTHER PUBLICATIONS

Sharafat et al., "Ceramic Foams: Inspiring New Solid Breeder Materials," 12th International Workshop on Ceramic Breeder Blanket Interactions, Germany, Sep. 16-17, 2004, 22 pages.
Supulveda et al., "Processing of Cellular Ceramics by Foaming and In Situ Polymerisation of Organic Monomers," Loughborough University, 1999, 22 pages.
Wires.co.uk, "Bare Nickel Chrome/Nichrome Section," Jun. 20, 2012, 33 pages.
Wires.co.uk, "Specialist in Craft Wire," Jun. 20, 2012, 5 pages.
Written Opinion for Application No. PCT/AT2009/000413, dated Jan. 25, 2010, 5 pages.
Written Opinion for Application No. PCT/AT2009/000414, dated Jan. 26, 2010, 14 pages.
Written Opinion for Application No. PCT/AT2012/000017, dated Jul. 3, 2012, 4 pages.
Written Opinion for Application No. PCT/GB2014/051633, dated Dec. 4, 2014, 11 pages.
Written Opinion for Application No. PCT/GB2014/051688, dated Aug. 26, 2014, 4 pages.
Written Opinion for Application No. PCT/GB2015/051213, dated Jul. 16, 2015, 9 pages.
Written Opinion dated Jun. 23, 2014 for Application No. PCT/EP2013/064922, filed Jul. 15, 2013, 4 pages.
Written Opinion of the International Preliminary Examining Authority for Application No. PCT/GB2015/050195 dated Jan. 20, 2016, 8 pages.
Written Opinion of the International Searching Authority for Application No. PCT/GB2015/050195, dated Sep. 2, 2015, 8 pages.
Written Opinion of the International Preliminary Examining Authority for International Application No. PCT/GB2015/051213 dated Mar. 29, 2016, 9 pages.
"Addictiveness and Attractiveness of Tobacco Additives", written procedure, European Commission Directorate-General for Health & Consumers, Scientific Committee on Emerging and Newly Identified Health Risks, SCENIHR , Jul. 6, 2010 , 112 pages.
"Bringing attention to e-cigarette pH as in important element for research and regulation", Tobacco Control, vol. 24, No. 4 , May 14, 2014 , 2 Pages.
"Certified Priority document of WO2015091258, Priority No. EP13198390.0, Priority date: Nov. 12, 2013".
"Chilean Office Action, Application No. 201701108, dated Aug. 20, 2018".
"Chilean Office Action, Application No. 201701137, dated Aug. 20, 2018".
"Chinese Office Action, Application No. 201580060720.X, dated Dec. 4, 2017".
"Chinese Search Report, Application No. 201580061121.X, dated Jan. 23, 2018".
"Consolidated list of citations—EP3214957", Nov. 19, 2019.
"Corrected Affidavit of Andrew Allan Burton", Submitted in Counterpart Application EP 3491941 , Oct. 15, 2021 , 8 Pages.
"Decision to Grant for Russian Application No. 2017105898, dated Mar. 16, 2018".
"Declaration by Connor Bruton dated Feb. 27, 2020 filed on the corresponding U.S. application, U.S. Appl. No. 15/525,194", some pages have been incorrectly labelled U.S. Appl. No. 15/525,163 , 8 pages.
"Declaration of Adam Bowen", Feb. 28, 2022.
"Declaration of Daniel Myers", Mar. 2, 2022.
"Declaration of John McKean", European Patent Application No. 15794254.1 (EP3214957B), Opposition: Nerudia Limited , Nov. 12, 2019 , 1 Page.
"Declaration of Joseph P. Hamilton", Hamilton Declaration , Nov. 8, 2019 , 7 Pages.
"Declaration of Marc Doring", Nov. 12, 2019.
"Declaration of Sara Luisa Mellor de Sousa", European Patent Application No. 15794254.1 (EP3214957B), Opposition: Nerudia Limited , Nov. 11, 2019 , 1 Page.
"Declaration of William Ward III", Feb. 28, 2022.
"eRoll pictures metadata", Nov. 11, 2019.
"European Patent Office Boards of Appeal Datasheet for the Decision for T405/13, Application No. 03077709.8", Apr. 9, 2014.
"European Search Report for Application No. 22155057.7, mailed on Jun. 15, 2022".
"Extended European Search Report for Application No. 19196432.9, mailed on Dec. 9, 2019".
"Extended European Search Report for Application No. 20183945.3, mailed Oct. 13, 2020".
"Extended European Search Report for European Application No. 18212381.0, mailed Apr. 15, 2019".
"Extraction from the Register of European Patents of 3082484 (WO2015091258) downloaded Dec. 11, 2019".
"Feature Analysis of Claim 1", BATMark Limited, Opposition Against EP3117860B1, Exhibit D6 , Oct. 30, 2019 , 1 Page (Official Copy Only).
"Federal Register", Federal Register Doc .99-7022 , Mar. 23, 1999 , pp. 14,086-14,096.
"Great Britain Search Report, Application No. GB1419865.9, dated May 7, 2015".
"Great Britain Search Report, Application No. GB1419866.7, dated May 7, 2015".
"Great Britain Search Report, Application No. GB1517361.0, dated Feb. 8, 2016".
"Health Risk of BPA in Ecig Products", ECF, https://www.e-cigarette-forum.com/threads/health-risk--of-bpa-in-ecig-products.443140/ , Jul. 16, 2013 , 4 Pages.
"International Preliminary Report on Patentability for Appl. No. PCT/GB2016/053051, mailed on Nov. 27, 2017".
"International Preliminary Report on Patentability, International Application No. PCT/GB2015/053368, mailed Feb. 3, 2017".
"International Preliminary Report on Patentability, International Application No. PCT/GB2015/053369, Mailed Oct. 7, 2016".
"International Search Report and Written Opinion, Application No. PCT/GB2016/053051, mailed Jan. 2, 2017".
"International Search Report and Written Opinion, International Application No. PCT/GB2015/053369, Mailed Feb. 5, 2016".
"International Search Report and Written Opinion, PCT/GB2015/053368, mailed Jan. 15, 2016".
"Japanese Decision to Grant, Application No. 2017-523309, dated Jul. 24, 2018".
"Japanese Office Action, Application No. 2017-523310, dated Apr. 10, 2018".
"Japanese Search Report, Application No. 2017-523310, dated Jan. 23, 2018".
"Juul Labs Delivery message", Messenger Receipt 2p—Ball, Krystine , Nov. 11, 2019 , 2 Pages.
"Korean Office Action, Application No. 10-2017-7012228, mailed Oct. 22, 2018".
"Korean Office Action, Application No. 10-2017-7012229, mailed Oct. 22, 2018".
"Letter Accompanying Corrected Affidavit of Andrew Allan Burton", Submitted in Counterpart Application EP 3491941 , Oct. 18, 2021 , 1 Page.
"Letter from Patentee for European Application No. 17189951.1, dated Aug. 21, 2018".
"Look What My Banana Juice Did To My Tank!", Planet of the Vapes, https://www.planetofthevapes.co.uk/forums/ecig-discussion/general-chat/threads/look-what-my-banana-juice-did-to-my-tank.3083/ , Sep. 22, 2012 , 6 Pages.
"Measuring pH of Non-Aqueous and Mixed Samples", Thermo Fisher Scientific, Application Note 007, document reference AN-PHNONAQS-E 1014 Rev A, 2014 , 4 Pages.
"Mil-G-45204 Military Specification: Gold Plating", Electrodeposited [S/S By MIL-DTL-45204D], Jun. 7, 1983 , 18 Pages.
"Notice of Allowance received for Korean Patent Application No. 10-2017-7012228, mailed on Apr. 28, 2019".
"Notice of Opposition—Imperial Tobacco Limited for European Application No. 20171293.2, mailed on Nov. 16, 2022".
"Notice of Opposition—Philip Morris for European Application No. 20171293.2, mailed on Nov. 17, 2022".
"Notice of Opposition mailed May 25, 2021 for European Application No. 15794253.3 (EP3214956)".

(56) References Cited

OTHER PUBLICATIONS

"Notice of Opposition to EP3214957 B1, filed by George W. Schlich, Nov. 13, 2019".
"Notice of Opposition to EP3214957, filed by Plate Schweitzer Zounek, Nov. 13, 2019".
"Notice of Reasons for Rejection for Japanese Application No. 2020-121265, mailed on Jun. 21, 2022".
"Notice of Reasons for Rejection received for Japanese Application No. 2020-181572 mailed on Feb. 14, 2023".
"Notice of Reasons for Rejection received for Japanese Patent Application No. 2020-121265, mailed on Apr. 11, 2023".
"Notification of First Office Action for Chinese Application No. 2018103833246, dated Jun. 3, 2020".
"Notification to Grant received for Chinese Patent Application No. 201610256674.7, mailed on Jan. 12, 2023".
"Observations on the Grounds of Appeal for European Patent No. 3214957 (15794254.1), mailed Apr. 14, 2022".
"Occupational Health Guideline for Nicotine", U.S. Department of Labor, Occupational Safety and Health Administration , Sep. 1978 , 6 Pages.
"Office Action For Korean Application No. 10-2018-7031081, mailed on Dec. 15, 2021".
"Office Action for Ukraine Application No. a201810662, mailed Jul. 22, 2022".
"Office Action mailed Aug. 5, 2020 for European Application No. 15794254.1".
"Office Action received for Canadian Patent Application No. 2,964,829, mailed on Jun. 5, 2023".
"Office Action received for Chinese Patent Application No. 2020105247754, mailed on Feb. 28, 2023".
"Office Action received for European Patent Application No. 16777777.0, mailed on Jun. 15, 2020".
"Opposition to EP3214957, filed by JT International, Bandpay & Greuter, Nov. 13, 2019".
"Opposition to EP3214957, filed by Nerudia Limited, Newburn Ellis", Nov. 13, 2019.
"Oral Proceedings for the Opposition of European Patent No. 3214957 (15794254.1), mailed Jun. 25, 2021".
"Picture of the atomizer of the "eRoll"", Nov. 11, 2019.
"Picture of the atomizer of the "eRoll"e-cigarette", Oct. 30, 2019.
"Picture of the atomizer of the "Wick of the eRoll E-Cigarette"", Nov. 10, 2019.
"QQ-S-365D Federal Specification: Silver Plating", Electrodeposited, General Requirements For , Jun. 3, 1985 , 12 Pages.
"Reply of the patent proprietor to the notice(s) of opposition Patent No. 3491941 (18212381 ), dated Oct. 7, 2021".
"Reply to Grounds of Appeal, for European Patent No. 3214957 (15794254.1), mailed Apr. 20, 2022".
"Report on determining the cartridge material of the eRoll E-Cigarette", Analysis of an eRoll cartridge, Annex D4c , Nov. 10, 2019 , 3 Pages.
"Response Filed in Opposition to European Patent No. 3214956 on Oct. 15, 2021".
"Results", May 11, 2019.
"Results", Apr. 11, 2019.
"Russian Office Action, Application No. 2018111280, dated Dec. 10, 2018".
"Screenshot of "Joyetech eRoll Manual"", Retreived from the Internet: URL: https://www.joyetech.com/download/?mid=1145 , Oct. 5, 2012 , 1 Page.
"Search Report for Japanese Application No. 2018-546893, mailed Nov. 25, 2019".
"Search Report mailed Jan. 21, 2020 for Chinese Application No. 201680056890.5".
"Search Report mailed Mar. 8, 2021 for Chinese Application No. 2019101103915".
"Sex, GABA, and Nicotine: The Impact of Smoking on Cortical GABA Levels Across the Menstrual Cycle as Measured with Proton Magnetic Resonance Spectroscopy", Biol Psychiatry , Jan. 1, 2005 , 12 Pages.

"Signed Affidavit of Andrew Allan Burton", Submitted in Counterpart Application EP 3491941 , Oct. 7, 2021 , 8 pages.
"The E-Cigarette Industry, Waiting to Exhale", Wayback Machine archive of Article in New York Times: https://www.nytimes.com/2013/10/27/business/thee-cigarette-industry-waiting-to-exhale.html., NY Times article dated Oct. 26, 2013, XP055656051 , Oct. 28, 2013 , 12 Pages.
"The Vapor Pro", available at URL: https://web.archive.org/web/20140223102416/http://www.thevaporpro.com/faq.html. , Feb. 23, 2014 , 27 Pages.
"Wayback Machine archive of The Vapor Pro", website: http://www.thevaporpro.com/faq.html , Sep. 11, 2013 , 19 Pages.
"Wikipedia entry for Lik Hon", https:/ /en.wikipedia.org/wiki/Hon Lik , Oct. 18, 2019 , 4 Pages.
"Witness Statement Noori Brifcani", May 6, 2021.
"Written Opinion of International Preliminary Examining Authority, International Application No.: PCT/GBZ015/053368, mailed Oct. 4, 2016".
"Written Opinion, Application No. PCT/GBZ016/053051, mailed Aug. 16, 2017".
Amsterdam , "Contribution of monoamine oxidase (MAO) inhibition to tobacco and alcohol addiction", Life Sciences, vol. 79, No. 21 , 2006 , pp. 1969-1973.
Armitage AK, D K Turner , "Absorption of nicotine in cigarette and cigar smoke through the oral mucosa", Nature, 226 , 1970 , pp. 1231-1233.
ASTM , "Standard Specification for Electrodeposited Coatings of Gold for Engineering Uses", B488-11 , 2011 , 6 Pages.
Barsanti KC , et al. , "Tobacco smoke particulate matter chemistry by NMR", Magnetic Resonance in Chemistry, vol. 45 , 2007 , pp. 167-170.
Berlin, I.; M. Anthenelli, R. , "Monoamine oxidases and tobacco smoking", The International Journal of Neuropsychopharmacology, vol. 4, No. 1, doi:10.1017/SI461145701002188. PMID 11343627 , 2001 , pp. 33-42.
Bowen , et al. , "U.S. Appl. No. 61/912,507, filed on Dec. 5, 2013".
Britton M , et al. , "Impact of Health Technology Assessments, Some Experiences of SBU", Int J Technol Assess Health Care, vol. 18, No. 4 , 2002 , pp. 824-831.
Chakraborty S , "Mediated Electrocatalytic Oxidation of Bioanalytes and Biosensing of Glutamate using Functionalized Multiwall Carbon Nanotubes-biopolymer Nanocomposite", Journal of Electroanalytical Chemistry, vol. 609, No. 2 , Nov. 1, 2007 , pp. 155-162.
Clayton , et al. , "Spectroscopic Investigations into the Acid-base Properties of Nicotine at Different Temperatures" , Analytical Methods. RSC Publishing, vol. 5 , 2013 , pp. 81-88.
Clayton P M , et al. , "Use of chiroptical spectroscopy to determine the ionisation status of (S)-niotine in e-cigarette formulations and snus", ST49, Coresta Congress, Quebec City, Canada, Available at: http://www.bat-science.com/groupms/sites/BAT_9GVJXS.nsf/vwPagesWebLive/DO9PVC3G/$FILE/CORESTA_PC_2014.pdf. , Oct. 12-16, 2014 , 16 Pages.
Cymes G D , "The Unanticipated Complexity of the Selectivity—Filter Glutamates of Nicotinic Receptors", Nature Chemical Biology, vol. 8, No. 12 , Dec. 2012 , pp. 975-981.
Dankwa , et al. , "Aids to Smoking Cessation", New Zealand Medical Journal, vol. 110, No. 1041 , Apr. 11, 1997 , pp. 131-132.
Deals or Duds , "Why Do Some E-liquids Crack Plastic Tanks?", Retrieved from the Internet: https://www.dealsorduds.com/guides/e-liquids-crack-plastic-tanks/ , Apr. 26, 2014 , 14 Pages.
Dongmei , et al. , "Catalytic Mechanism of Cytochrome P450 for 5'-Hydroxylation of nicotine: Fundamental Reaction Pathways and Stereoselectivity", Journal of American Chemical Society, vol. 133, No. 19 , May 18, 2011 , pp. 7416-7427.
Duell AK. , et al. , "Free-base Nicotine Determination in Electronic Cigarette Liquids by 1 H NMR Spectroscopy", Chemical Research in Toxicology, vol. 31 , 2018 , pp. 431-434.
Durazzo T C , "Chronic Cigarette Smoking in Alcohol Dependence: Associations with Cortical Thickness and N-Acetylasparate Levels in the Extended Brain Reward System", Addict Biology, vol. 18, No. 2 , Mar. 2013 , pp. 379-391.

(56) References Cited

OTHER PUBLICATIONS

Ei-Hellani A, et al., "Quantification of free-base and protonated nicotine in electronic cigarette liquids and aerosol emissions", Chemical Research in Toxicology, vol. 28, No. 8, Aug. 17, 2016, pp. 1532-1537.
EV, Stockel, "Technical Report", Jun. 24, 2021, 1 Page.
Fowler, et al., "Brain monoamine oxidase A inhibition in cigarette smokers", Proceedings of the National Academy of Sciences of the United States of America, vol. 93, No. 24, Nov. 1996, pp. 14065-14069.
Fowler, et al., "Inhibition of monoamine oxidase B in the brains of smokers", Nature, vol. 379, Feb. 22, 1996, pp. 733-736.
Fox, Lindsay, "10 Coolest E-Cig Mods, ecigarettes", available from http://ecigarettereviewed.com/coolest-e-cigs-mods, retrieved on Nov. 15, 2016, 18 Pages.
Giannos S A, "Temporally Controlled Drug-Delivery Systems—Coupling of pH Oscillators with Membrane-Diffusion", Journal of Pharmaceutical Sciences, vol. 84, No. 5, May 1995, pp. 539-543.
Glueck C J, "Nonpharmacologic and Pharmacologic Alternation of High-Density Lipoprotein Cholesterol: Therapeutic Approaches to Prevention of Atheroschlerosis", Am Heart Journal, vol. 110, No. vol. 110, No. vol. 110, No. 5, Nov. 1985, pp. 1107-1115.
Henningfield J.E., et al., "Estimation of available nicotine content of six smokeless tobacco products", Tobacco Control, vol. 4, 1995, pp. 57-61.
JoyeTech, "eGo-C Atomizer body", Retrieved from the Internet: https://www.joyetech.com/producl/ego-c-atomizer-body/, 2019, 3 Pages.
JoyeTech, "eGo-C Atomizer head", Retrieved from the Internet: https://www.joyetech.com/producl/ego-c-atomizer-headl, 2019, 2 Pages.
JoyeTech, "eGo-C Starter Kits", Retreived from the Internet: https://www.joyetech.com/producl/ego-c-starter-kit/, 2019, 3 Pages.
JoyeTech, "eGo-T A Type Transparent Empty Cartridge (5Pcs)", Retrieved from the Internet: https://www.oyetech.com/producl/ego-t-a-type-transparent-empty-cartridge5pcs/, 2019, 2 Pages.
JoyeTech, "eRoll Battery", Retreived from the Internet: https://www.joyetech.com/producl/eroll-battery/, 2019, 2 Pages.
JoyeTech, "e-roll Empty Cartridge", Retreived from the Internet: https://www.joyetech.com/producl/eroll-empty-cartridge/, 2019, 2 Pages.
JoyeTech., "Edited Drawing and translation", Shenzhen Jianyiteke Science & Technology Co Ltd, translation Apr. 14, 2021, Oct. 19, 2012, 2 Pages.
JoyeTech, "e-roll Starter Kits", Retrieved from the internet: https://www.joyetech.com/producl/eroll-starter-kil/, 2019, 4 Pages.
JoyeTech, "eRoll Starter Kit", eRoll series, E-Cigarette, Printout Wayback Machine for the webpage: http://www.joyetech.com/product/details.php?gno-123, Oct. 26, 2014, 4 Pages.
JWEI Group, "About JWEI", downloaded May 5, 2021, 2019, 3 Pages.
JWEI Group., "Zoominfo", downloaded May 5, 2021.
Kalantari-Dehaghi M, et al., "Mechanisms of Mitochondrial Damage in Keratinocytes by Pemphigus Vulgaris Antibodies", Journal of Biological Chemistry, vol. 288, No.23, Jun. 7, 2013, pp. 16916-16925.
Keithl, et al., "Industry research on the use and effects of levulinic acid: a case study in cigarette additives", Nicotine Tobacco Research, vol. 7, No. 5, Oct. 2005, pp. 761-771.
Kovacic, et al., "Iminium Metabolite Mechanism of Nicotine Toxicity and Addiction: Oxidative Stress and Electron Transfer", Medical Hypotheses. vol. 64, No. 1, 2005, pp. 104-111.
Leffingwell, "Leaf Chemistry BA Basic Constituents of Tobacco Leaf and Differences among Tobacco Types", Blackwell Science XP055326787. Retrieved from the Internet: URL: http: www.leffingwell.com/download/Leffingwell- Tobacco production chemistry and technology.pdf., Jan 1, 1999, pp. 265-284.
LiteCig, USA, "Orders and Confirmations", 2013, 13 Pages.
Mashhoon, et al., "Anterior Cingulate Proton Spectorscopy Glumate Levels Differ as a Function ofSmoking Cessation Outcome", Prog Neuropsychoparmacol Biol Psychiatry, vol. 35, No. 7, Aug. 15, 2011, pp. 1709-1713.
McAdam, et al., "Application and File History for U.S. Appl. No. 15/525,194, filed May 8, 2017".
McAdam, et al., "Application and File History for U.S. App. No. 15/764,612, filed Mar. 29, 2018".
McAdam, et al., "Application and File History for U.S. Appl. No. 15/525,163, filed May 8, 2017".
Morie G P, "Fractions of protonate and unprotonated nicotine in tobacco smoke at various pH", Tobacco Science, 56 (ISSN: 0082-4623)., 1972, p. 167.
Newton, et al., "New OTC drugs and Devices 2002, a Selective Review", J Am Pharm Assoc, vol. 44, No. 2, Mar.-Apr. 2004, pp. 211-225.
O'Neill, et al., "Thalamic Glutamate Decreases with Cigarette Smoking", Psychopharmacology, (Berlin), Feb. 18, 2014, Epub ahead of print), vol. 231, No. 13, Jul. 2014, pp. 2717-2724.
Pankow J F, "Conversion of Nicotine in Tobacco Smoke to its Volatile and Available Free-Base Form Through the Action of Gaseous Ammonia", Environmental Science & Technology, vol. 31, No. 8, Aug. 1997, pp. 2428-2433.
Pankow J F, "Percent Free Base Nicotine in the Tobacco Smoke Particulate Matter of Selected Commercial And Reference Cigarettes", Chemical Research in Toxicology, vol. 16, No. 8, Aug. 2003, pp. 1014-1018.
Perfetti T A, "Structural Study of Nicotine Salts", Beitrage zur Tabakforschung International, vol. 12, No. 2, Jun. 1983, pp. 43-54.
Petrov, et al., "Two-electron transfer reactions in proteins: bridge-mediated and proton- assisted processes", Phys Rev E Stat Nonlin Soft Matter Phys, vol. 68, part 1, Jun. 19, 2016, epub Dec 31 2003., Dec. 2003, 2 pages.
Poindexter, et al., "The isolation of harmane and norharmane from tobacco and cigarette smoke", Phytochemistry, vol. 1, No. 3, 1962, pp. 215-221.
Pongjanyakul, et al., "Alginate-magnesium aluminium silicate films for buccal delivery of nicotine", Colloids and Surfaces B: Biointerfaces, vol. 74, 2009, pp. 103-113.
Pongjanyakul, et al., "Influence of pH modifiers and HPMC viscosity grates on nicotine- magnesium aluminium silicate complex loaded buccal matrix tablets", AAPS PharmSciTech, Vo. 13. No. 2, 2012, pp. 674-685.
Sae, "AMS 2410K Plating, Silver", Nickel Strike, High Bake, Apr. 19, 2010, 4 Pages.
Sae, "AMS 2411H Plating, Silver", for High Temperature Applications, Dec. 17, 2013, 4 Pages.
Sae, "AMS 2412K Plating, Silver", Copper Strike, Low Bake, Jan. 26, 2015, 4 Pages.
Sastri, V.R., "Plastics in Medical Devices: Properties, Requirements and Applications", 2010, pp. 100,226,230.
Seeman, et al., "The Form of Nicotine in Tobacco. Thermal Transfer of Nicotine and Nicotine Acid Salts to Nicotine in the Gas Phase", in J Agric Food Chern, vol. 47, 1999, pp. 5133-5145.
Spinefuel, "Smoktech 510 Screw Tank & 510 Pro DCTank Combo Review". https://spinfuel.com/smoktech-51 0-screw-tank-510-pro-dctank-combo-review/, Sep. 28, 2012, 4 Pages.
VAPEGRL, "Silver and Gold E-cigarettes", vapegrl.com, Available from: http://vapegrl.com/silver-gold-e-cigarettes/, Feb. 15, 2016, 8 Pages.
VAPERANKS, "Luxury Customization Company Launches 24ct-Gold-Plated E-Cigarettes", vaperanks.com, as available from: http://vaperanks.com/luxury-customization-company-launches-24ct-gold-plated-e-cigarette/, Feb. 4, 2016, 3 Pages.
Vapordna, "Buy Online Electronic Cigrettes and Accesseories at the Best Possible Prices", https://vapordna.wordpress.com/, Sep. 9, 2014, 12 Pages.
Vas, et al., "Acetoin is a precursor to diacetyl in e-cigarette liquids", Food and Chemical Toxicology, vol. 133, 110727, 2019, 16 pages.
Villegier, et al., "Transient behavioral sensitization to nicotine becomes long-lasting with monoamine oxidases inhibitors", Pharmacol. Biochem. Behav., vol. 76, No. 2, Sep. 2003, pp. 267-274.

(56) References Cited

OTHER PUBLICATIONS

Vlachou, et al., "Both GABA(B) receptor activation and blockage exacerbated anhedonic aspects of nicotine withdrawal in rats", Eur J Pharmacol., vol. 655, No. 1-3, Mar. 25, 2011, pp. 52-58.
Ward, William, "Pictures of the "eRoll Battery"", Juul, email Nov. 11, 2019, 7 Pages.
Wikipedia, "Electronic Cigarette", Available at <https://en.wikipedia.org/w/index.php?title=Electronic_cigratte&oldid=284227163>, Apr. 16, 2009, 7 Pages.
Yao, Jason, "Email from Jason Yao", Mar. 16, 2021, 1 Page.
Zhang, et al., "Quantitative Analysis of Six Heterocyclic Aromatic Amines in Mainstream Cigarette Smoke Condensate Using Isotope Dilution Liquid Chromatography—Electrospray Ionization Tandem Mass Spectrometry", Nicotine & Tobacco Research vol. 13, No. 2, doi: 10.1093/ntr/ntq219., 2010, pp. 120-126.
"Shenzhen Jianyiteke Science & Technology Co Ltd", Oct. 19, 2012, 1 Page.
ASTM, "B700-8 Standard Specification for Electrodeposited Coatings of Silver for Engineering Use", 2014, 5 Pages.
Barr P., "Technical Analysis of Joyetech eRoll cartridge and Joyetech eGo-C cartridge", Nov. 12, 2019, 3 Pages.
EV Stockel, "Technical Report", Nov. 8, 2019, 3 Pages.
EV Stockel, "Technical Report on Absorption Behaviour of Protonated Nicotine", Jul. 9, 2020, 5 Pages.
GoldGenie, "A 24 carat gold-plated electronic cigarette E-cigarette reviews and rankings", Feb. 17, 2014, 6 Pages.
JoyeTech, "The eRoll—User Manual", Oct. 5, 2012, 9 Pages.
Matt, Richtel, "The E-Cigarette Industry, Waiting to Exhale", New York Times, Oct. 26, 2013, 8 Pages.
Patel, "Structural studies of Impatiens balsamina antimicrobial protein (Ib- AMPI)", Biochemistry, vol. 37, No. 4, Jan. 27, 1998, pp. 983-990.
Pinggera, et al., "Urinary acetonitrile concentrations correlate with recent smoking behaviour", BJU International, vol. 95, No. 3, Sep. 20, 2004, pp. 306-309.
Sae, "AMS 2422F Plating, Gold", Feb. 6, 2014, 2 Pages.
Sami, "Studies on electron transfer reactions of Keggin-type mixed addenda heteropolytungstovanadophosphates with NADH", Journal of Chemical Sciences, vol. 121, No. 2, Mar. 2009, pp. 155-161.
Tripathi, D., "Practical Guide to Polypropylene", Rapra Technology Ltd, 2002, pp. 98-99.
Notification of Grant received for CN Appln. No. 2016102566747, mailed Jan. 12, 2023, 7 pages.

* cited by examiner

INHALER COMPONENT

RELATED APPLICATION

This application is a continuation of application Ser. No. 15/997,113, filed Jun. 4, 2018, which in turn is a continuation of application Ser. No. 14/268,909 filed May 2, 2014, now U.S. Pat. No. 10,010,695 issued Jul. 3, 2018, which in turn is a continuation of application Ser. No. 13/984,512, filed Aug. 29, 2013, now U.S. Pat. No. 8,752,545 issued Jun. 17, 2014, which is the national stage entry of International Application No. PCT/AT2012/000017, filed Feb. 2, 2012, which in turn claims priority to Austrian Patent Application No. A187/2011, filed Feb. 11, 2011, and to Austrian Patent Application No. A1095/2011, filed Jul. 27, 2011, each of which is hereby fully incorporated herein by reference.

FIELD

The invention relates to an inhaler component for the formation of a vapor-air mixture or/and of a condensation aerosol by evaporating a liquid material and, if necessary, condensing the vapor formed, comprising: a heating element for the evaporation of a portion of the liquid material; a wick for the automatic supply of the heating element with the liquid material, the said wick having at least two end sections arranged at a distance from each other; a first capillary gap for the automatic supply of the wick with the liquid material, wherein a first end section of the wick extends into the first capillary gap.

BACKGROUND

Definition of terms: In the present patent application the term "inhaler" refers to medical as well as non-medical inhalers. The term refers furthermore to inhalers for the administration of drugs and materials which are not declared as drugs. The term refers, in addition, to smoking articles and cigarette substitutes, such as those in European patent class A24F47/00B, for example, as far as these are intended to supply the user with a vapor-air mixture or/and a condensation aerosol. The term "inhaler" also implies no restrictions on how the vapor-air mixture or/and condensation aerosol formed is supplied to the user or his body. The vapor-air mixture or/and condensation aerosol can be inhaled into the lungs or, in addition, only supplied to the oral cavity—without inhalation into the lungs.

"Capillary gap" means any gap which causes liquid transport solely on the basis of the capillary action of its confining walls. Wicks, wrapped wicks or channels filled with wick material are not capillary gaps.

WO 2010/045671 (Helmut Buchberger) describes an inhaler component for the intermittent, inhalation or pull-synchronous formation of a vapor-air mixture or/and condensation aerosol, consisting of (FIGS. 9 to 12 and FIGS. 17 to 18) a housing 3, a chamber 21 provided in the housing 3, an air intake opening 26 for the supply of air from the environment into the chamber 21 and an electric heating element for the evaporation of a portion of a liquid material 16, in which case the vapor formed mixes in the chamber 21 with the air supplied by the air intake opening 26 and the vapor-air mixture or/and condensation aerosol is or are formed. Furthermore, the inhaler component comprises a wick with a capillary structure, which wick forms with the heating element a laminar composite 22 and automatically resupplies the heating element with the liquid material 16 after evaporation. At least one heated section of the composite 22 is arranged without contact in the chamber 21 and the capillary structure of the wick lies exposed to a large extent in the said section at least on one side 24 of the laminar composite. One end of the laminar composite 22 projects into a capillary gap 41, which is coupled or is capable of being coupled by capillary to a liquid container 4 containing the liquid material 16. The capillary gap 41 draws the liquid material 16 from the liquid container 4 and conveys it to the wick.

After evaporation or inhalation the user of the inhaler component must observe a waiting period, during which the liquid material 16 can again completely infiltrate the wick. Evaporations before the expiration of the waiting period can lead to various disadvantageous consequences, for example a decrease in the given aerosol quantity or/and a local overheating of the wick, possibly associated with a decomposition of the liquid material and a degradation of the organoleptic characteristics of the vapor-air mixture or aerosol formed. In prototypes based on highly diluted ethanol or/and aqueous nicotine solutions, it was possible to obtain complete infiltration of the wick within 10 s. If the inhaler component is used as a cigarette replacement, then a waiting period of 10 s may be acceptable for many smokers; for some smokers, however, it may be too long. Furthermore, with the same prototypes it has been shown that even when the waiting period mentioned is adhered to, disturbances of the infiltration can occur. These disturbances rarely arise, but can lead to the same disadvantageous consequences as described above. The disturbances are characterized by an unsatisfactory wetting of the capillary structure of the wick by the liquid material and occur preferably locally, in regions of the wick which are peripheral in relation to the capillary gap.

SUMMARY

The object of the invention is to remedy the aforementioned disadvantages of the arrangement known from the state of the art. More particularly, it is the object of the invention to design an inhaler component of the type described in the preamble in such a way that the wick is infiltrated with the liquid material as rapidly as possible and no unpleasantly long waiting periods occur. Local disturbances of the infiltration are likewise to be avoided. All of this is to be achieved, if possible, without additional structural outlay. The production costs of the inhaler component should likewise not be increased.

This object is achieved by the characterizing features of claim 1. Accordingly, the inhaler component is provided with a second capillary gap, which holds the second end section of the wick. The wick is thus supplied with the liquid material from two sides. As a result, the waiting period for complete infiltration of the wick can be at least halved as compared with a conventional one-sided supply. If one considers that the infiltration of the wick with the liquid material takes place in a degressive-proportional manner, i.e. comparatively rapidly at the beginning and then more slowly, then it becomes clear that the waiting period for complete infiltration of the wick by the arrangement according to the invention can be shortened by significantly more than 50%. Similarly advantageous effects result regarding the security of supply of the wick: the particularly endangered regions of the wick on the periphery in relation to the first capillary gap can now be reliably supplied with the liquid material over a short distance from the second capillary gap.

In a preferred embodiment of the invention it is provided that the first and second capillary gaps are connected to each other by a third capillary gap. The first and second capillary gaps thus communicate with each other via the third capillary gap. Thus any uneven supply of the first and second capillary gap with the liquid material can be equalized, and the security of supply to the wick further improved.

It is further provided according to the invention that one of the capillary gaps is coupled or capable of being coupled by capillary to a liquid container containing the liquid material. This capillary gap can for example be the first capillary gap. In this case the second capillary gap would be supplied with the liquid material exclusively via the third capillary gap. In addition, it could alternatively be provided that the third capillary gap is coupled or capable of being coupled by capillary to the liquid container. In this case the first and second capillary gaps would be supplied with the liquid material via the third capillary gap.

Conditions which are particularly simple structurally result if all the capillary gaps are situated in a common plane. A further structural simplification is obtained by all the capillary gaps being formed by a board, preferably a printed circuit board, and an upper section mounted on the board. In this case only two components are required to form all the capillary gaps.

In a first variant of embodiment the upper section has, according to the invention, a recess facing the board. The recess forms the capillary gaps in co-operation with the surface of the board, the depth of the recess setting the width of the capillary gaps. It is particularly advantageous for the recess to be bounded at least locally by one or more ventilation grooves. The ventilation grooves have the advantageous effect that the liquid material stored in the capillary gaps can be used more effectively as buffer volumes.

In a second alternative variant of embodiment the upper section is mounted on the end sections of the wick. The end sections of the wick act in this case as spacers which set the width of the capillary gaps. In this alternative variant of embodiment too, the upper section would be considered as being "mounted on the board", even if the two components do not touch each other directly.

The board is preferably designed in the form of a printed circuit board and it serves as such for supplying electrical energy to the—in this case—electric heating element. In this case it is particularly advantageous for the printed circuit board to be designed in the form of a multiple-layer, so-called multilayer, printed circuit board. As a result, the conductive strips supplying the electric current can in this case be concentrated in layers which do not affect the capillary gaps. In addition, more complex arrangements of conductive strips can also be implemented by means of multilayer printed circuit boards, a circumstance which proves advantageous at the latest when a plurality of electric heating elements are provided, and the heating elements are to be actuated independently of one another. Finally, on account of the multiple-layer arrangement of their conductive strips, multilayer printed circuit boards allow comparatively high electric currents to be transmitted.

In a further arrangement of the invention it is provided that the first capillary gap is coupled or is capable of being coupled to a first liquid container containing the liquid material and the second capillary gap is coupled or is capable of being coupled to a second liquid container containing the liquid material. By providing two liquid containers essentially independent of each other the security of supply of the wick with the liquid material can once again be increased.

Expedient and advantageous embodiments of the invention are illustrated in the drawings and are explained in greater detail in the following description.

DETAILED DESCRIPTION

Figure 1:
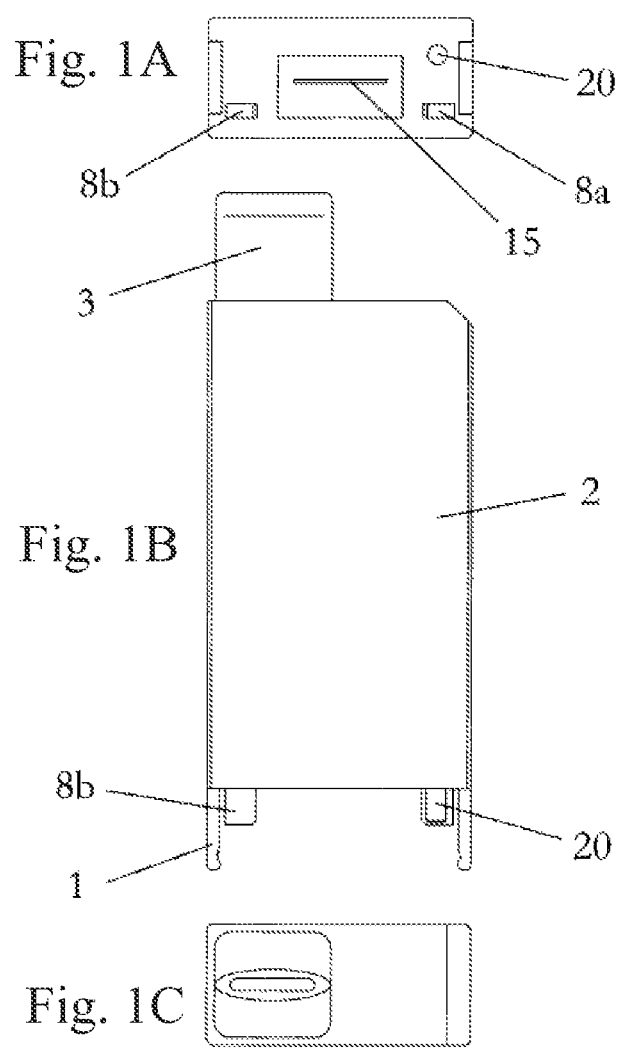
FIG. 1A shows a bottom view of an exemplary inhaler component according to the invention.
FIG. 1B shows a front view of an exemplary inhaler component according to the invention.
FIG. 1C shows a top view of an exemplary inhaler component according to the invention.

FIGS. 1A through 1C show multiple views of a first embodiment of an inhaler component according to the invention. The inhaler component in the specific example is designed in the form of an interchangeable part of the inhaler and is capable of being coupled via a snap connection 1 to a reusable inhaler part (not further shown). The inhaler component together with the reusable inhaler part forms the inhaler. The inhaler component consists of a housing 2 and further comprises a mouthpiece 3, by way of which the user of the inhaler draws the vapor-air mixture or/and the condensation aerosol.

FIGS. 2 to 5 provide further information about the internal structure of the inhaler component. Thus a carrier plate 4, which is preferably designed as a printed circuit board, is located in the housing 2. The printed circuit board 4 carries a laminar composite 5. The laminar composite 5 consists of a wick 7 and an electric heating element 6, which are connected to each other in a laminar manner or integrated one into the other. The laminar composite 5 can be formed for example by a metal foil with metal fabric layers sintered on it. The laminar composite 5 can alternatively also consist of an open-pored metal foam. The open-pored capillary structure of the fabric layers sintered onto the metal foil or the metal foam forms the wick 7 and the electrical resistance of the metal forms the heating element 6. Suitable metallic resistance materials are, for example, high-grade steels such as AISI 304 or AISI 316 as well as heat-conducting alloys, in particular NiCr alloys.

The wick 7 and the laminar composite 5 containing it have two end sections 7a and 7b arranged at a distance from each other. The laminar composite 5 is mounted with these end sections on the printed circuit board 4. The laminar composite 5 is furthermore electrically contacted in the region of the end sections 7a and 7b on conductive strips of the printed circuit board 4. The electrical contacting of the laminar composite 5 or the resistance heating element 6 thereof mat, for example, consist of an adhesive joint by means of an electrically conducting adhesive, for example, by means of a silver-containing adhesive based on epoxide. The printed circuit board 4 projects from the outside surface of the housing 2 in the form of two plug contacts 8a and 8b. The two plug contacts 8a and 8b serve to introduce the electrical energy into the inhaler component. The electrical energy is supplied to the electrical resistance heating element 6 via conductive strips of the printed circuit board 4. The printed circuit board 4 is preferably designed in the form of a multiple-layer, so-called multilayer, printed circuit board. The conductive strips are thus present in several layers. The advantages of this special type of printed circuit board have already been described above. The electrical energy is preferably drawn from the reusable inhaler part. For this purpose the reusable inhaler part contains a battery and an electrical control circuit for controlling the energy supply.

An upper section 9 having a recess or depression 10 is placed flat on the printed circuit board 4—see FIGS. 3 to 8B. The recess 10 is shown as a black area in FIG. 8B and has a depth of typically 0.2 mm. The recess 19 faces the printed circuit board 4 and, in conjunction with the surface thereof, forms a capillary gap. The capillary gap is shown diagrammatically in FIG. 2 as a black area and consists of three sections: a first capillary gap 11a, into which the laminar composite 5 or wick 7 with its end section 7a projects; a second capillary gap 11b, into which the laminar composite 5 or wick 7 with its end section 7b projects; and a third capillary gap 11c, which connects the first capillary gap 11a to the second capillary gap 11b. The first capillary gap 11a is connected to the liquid container 12 formed by the housing 2 or arranged in it. The liquid container 12 stores a liquid material 13. The capillary forces in the capillary gap 11a pull the liquid material 13 from the liquid container 12 into the capillary gap 11a. The liquid material 13 first reaches the end section 7a of the laminar composite 5.

There the liquid material 13 moistens the capillary structure of the wick 7, after which the wick 7 can be further infiltrated from this side with liquid material 13. In parallel with this the liquid material 13 flows into the capillary gap 11c and finally arrives by way of the latter at the capillary gap 11b, where in the end section 7b it again moistens the capillary structure of the laminar composite 5 or the wick 7. The wick 7 is thus infiltrated from two sides with the liquid material 13. Since the flow resistance of the capillary gaps is substantially lower than the flow resistance of the wick 7, the infiltration of the wick 7 takes place at almost the same time or symmetrically on both sides. Compared with arrangements with only one-sided supply of the wick 7 (see WO 2010/045671) the infiltration time can be substantially reduced.

After the wick 7 or laminar composite 5 has been completely infiltrated with the liquid material 13, the electrical energy can be supplied to the electrical resistance heating element 6 by way of the conductive strips of the printed circuit board 4 and the liquid material 13 evaporated. TO ensure as far as possible that the conductive strips do not affect the capillary gaps, it is advantageous if the conductive strips are arranged primarily on the back of the printed circuit board 4 and, if necessary, in intermediate layers (multilayer printed circuit board), and the individual conductive strips interconnected appropriately according to the state of the art by means of so-called plated-through holes. The vapor released is mixed in a chamber 14 provided in the housing 2 with the air supplied from the environment through an air intake opening 15 (see FIGS. 3 to 5) and forms the vapor-air mixture or/and condensation aerosol, which can then be transferred to a user via the mouthpiece 3.

Figure 2:
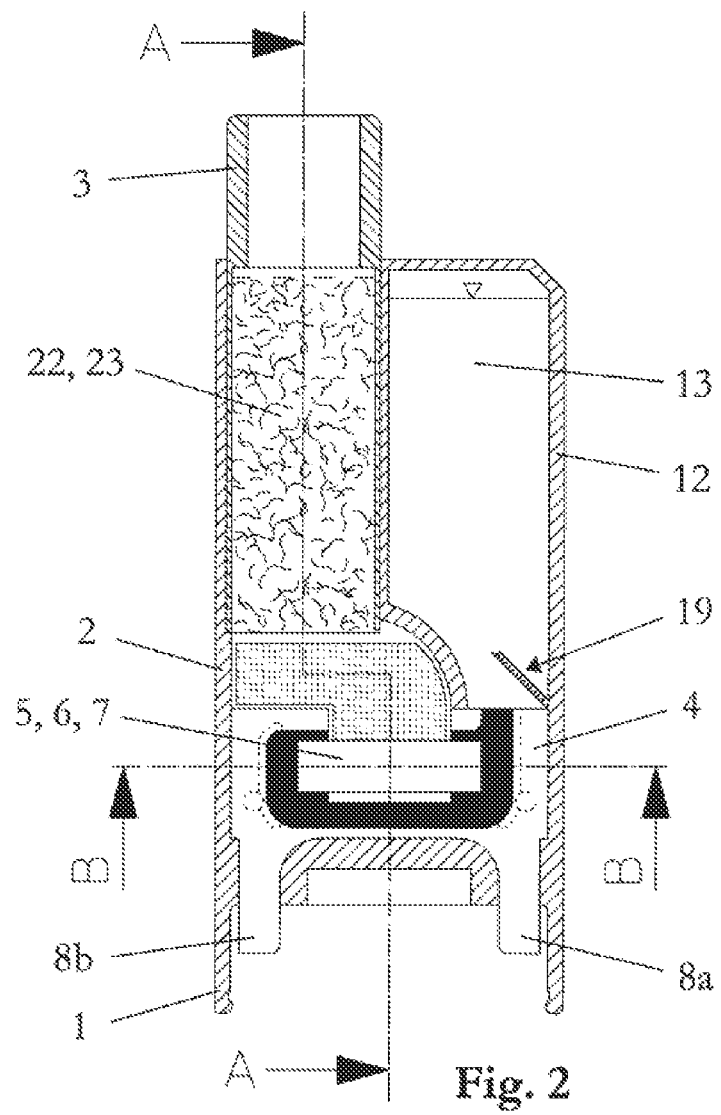
FIG. 2 is a longitudinal section through the inhaler component according to FIG. 1B at the level of the laminar composite.
Figure 4:
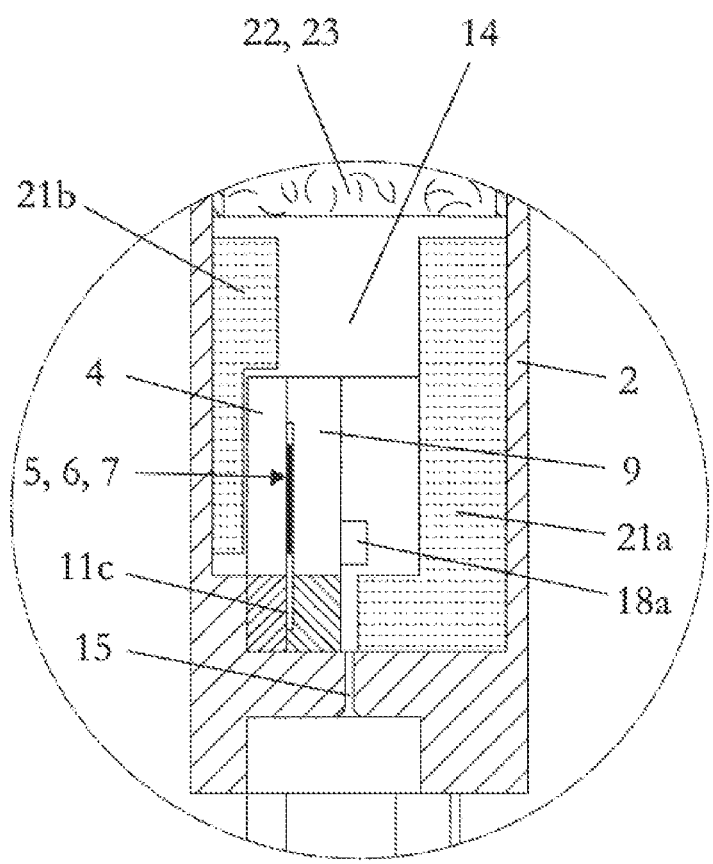
FIG. 4 shows the detail from FIG. 3 in an enlarged view.
Figure 5:
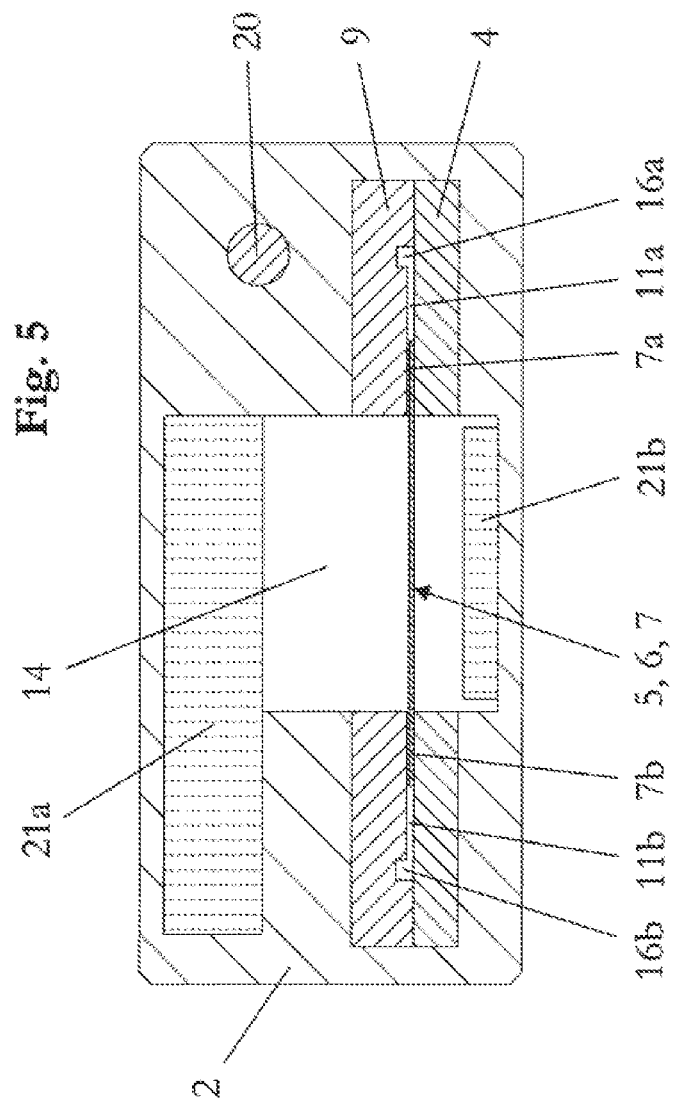
FIG. 5 is a cutaway view of the inhaler component along the line B-B in FIG. 2.
Figure 6:
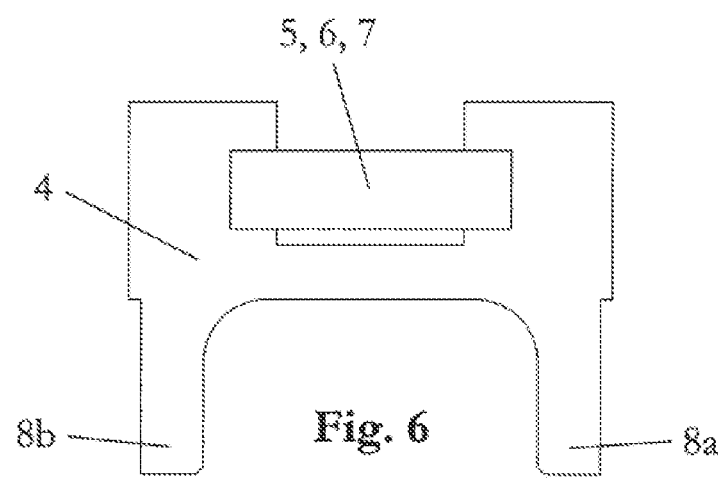
FIG. 6 shows the printed circuit board including a laminar composite.
Figure 7:
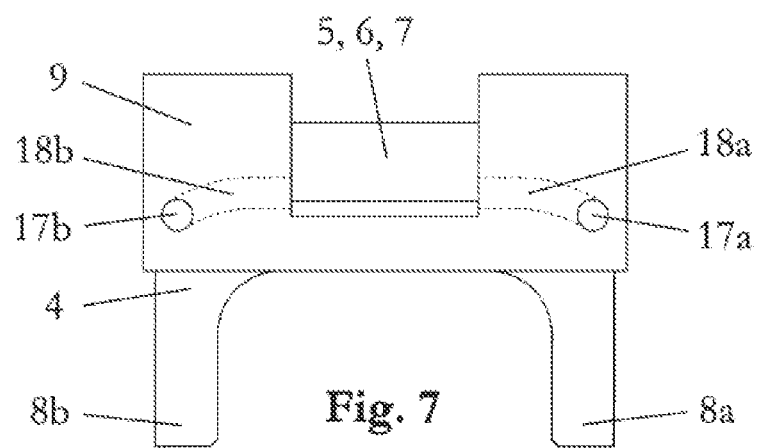
FIG. 7 shows the printed circuit board including a laminar composite joined to the upper section forming the capillary gaps.
Figure 8:
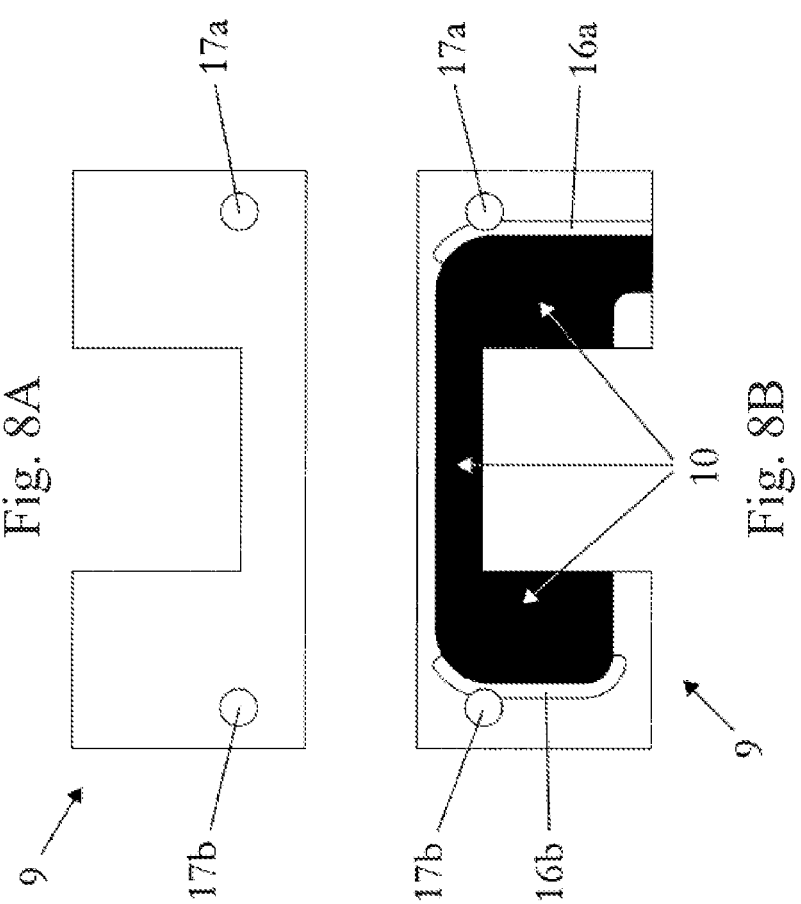
FIG. 8A shows a view of the upper section forming the capillary gaps.
FIG. 8B shows a further view of the upper section forming the capillary gaps, with the capillary gaps and recess visible.

In accordance with FIGS. 8A and 8B, the recess 10 in the upper section 9 is bounded in the region of the first capillary gap 11a by a first ventilation groove 16a and in the region of the second capillary gap 11b by a second ventilation groove 16b. In FIG. 2 the ventilation grooves 16a and 16b are represented diagrammatically as broken lines and in FIG. 5 are shown in cross-section. The ventilation groove 16a extends up to the liquid container 12 and ensures that each volume of liquid material 13 removed from the liquid container is replaced by an equivalent volume of air. The ventilation slots 16a and 16b draw in the air via ventilation holes 17a and 17b which are formed by the upper section 9 and which for their part are connected to the chamber 14 via connecting channels 18a and 18b formed by the housing 2. The connecting channels 18a and 18b are shown diagrammatically in FIG. 7 as broken lines. The outlet of the connecting channel 18a into the chamber 14 is shown in FIG. 4.

In principle, all known printed circuit board materials are suitable as the material for the printed circuit board 4, in particular the material types FR1 to FR5. The upper section 9 is added to the printed circuit board 4 by adhesive bonding and likewise consists preferably of a plastic. It is important that the surfaces of the printed circuit board 4 as well as of the upper section 9 are well moistened by the liquid material 13. It is preferable for highly diluted ethanol or/and aqueous solutions to be used as the liquid material 13, in which the actual active substances, aerosol-forming materials, flavorings, as well as, if necessary, further ancillary materials are dissolved or/and emulsified. The wettability as well as the adhesion of the plastics can be substantially improved by surface activation, for example by hydrophilization by means of plasma polymerization (the company Diener electronic GmbH+Co. KG, www.plasma.de).

Figure 9:
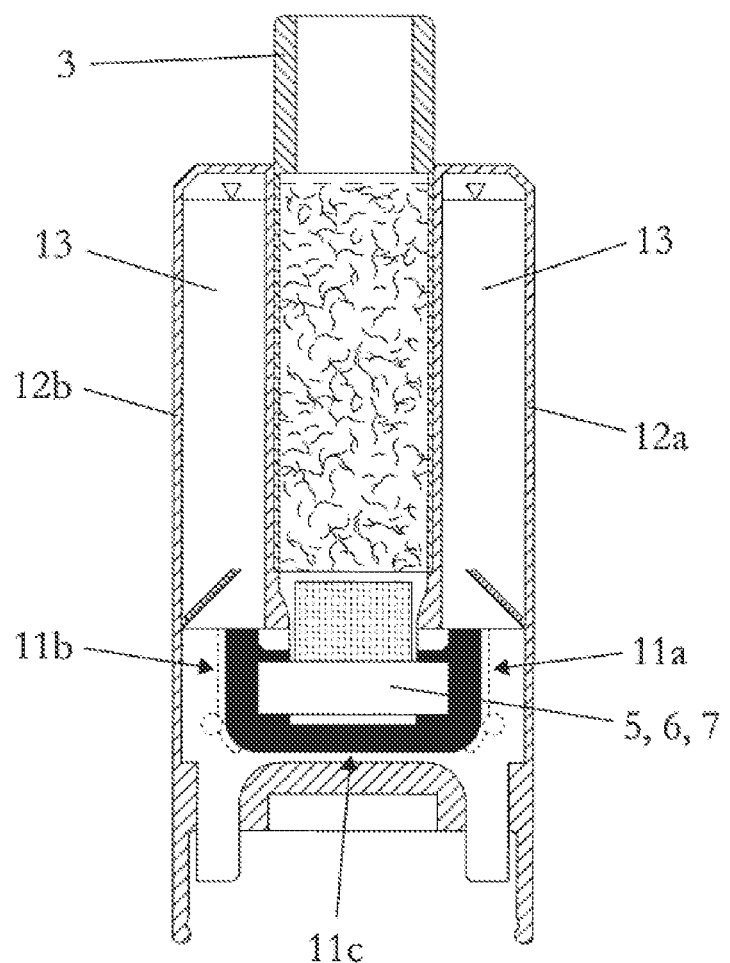
FIG. 9 shows an inhaler component according to the invention in an alternative embodiment in a view similar to FIG. 2.

FIG. 9 shows an alternative embodiment of the inhaler component according to the invention. This embodiment differs from the arrangement according to FIG. 2 essentially in that a second liquid container 12b containing the liquid material 13 is provided, which is coupled or is capable of being coupled to the second capillary gap 11b. If a disturbance of the liquid supply occurs in the first supply path (liquid container 12a and capillary gap 11a), then the laminar composite 5 or the wick 7 thereof can still be adequately supplied with liquid material 13 via the second supply path (liquid container 12b, capillary gap 11b and, if necessary, capillary gap 11c).

Figure 3:
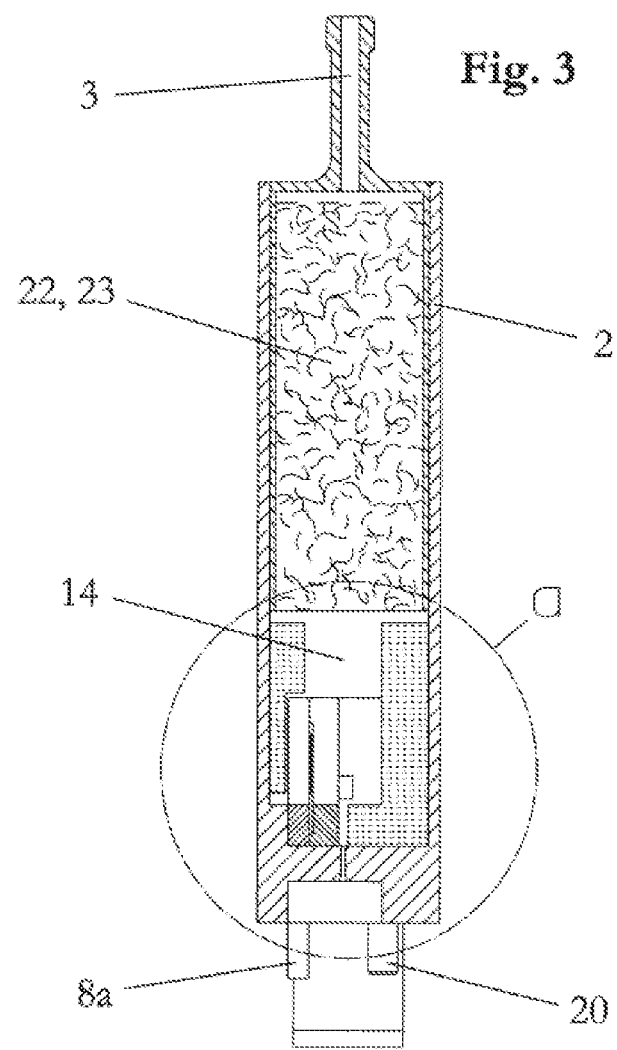
FIG. 3 is a cutaway view of the inhaler component along the line A-A in FIG. 2.

Still further components of the inhaler component are briefly described below. Even if these components are not directly relevant to the invention, their description nevertheless contributes to a better understanding of the function of the inhaler component according to the invention as a whole and ensures the workability of the invention still more certainly: as shown in FIG. 2, for example, the liquid container 12 has a valve-like, openable catch 19 on a front face. The openable catch 19 seals the liquid container 12 hermetically off from the exterior in its closed position. Only after opening the openable catch 19 can the liquid material 13 moisten the capillary gap 11a and then, through the action of capillary forces in the capillary gap, penetrate further to the laminar composite 5 and finally infiltrate the wick 7 of the laminar composite 5. The openable catch 19 is opened with the aid of a pin 20 mounted in the housing 2 in an axially adjustable manner (FIG. 3 and FIG. 5). A first end of the pin 20 is directed towards the openable catch 19. A second end extends from the outer surface of the housing 2 like an extension with the catch 19 still closed. The second end of the pin 20 is connected to the reusable inhaler part in a tappet-like operating condition. In the course of the coupling of the inhaler component with the reusable inhaler part the pin 20 is shifted into the housing 2, as a result of which the first end of the pin 20 presses against the openable catch 19. The openable catch 19 has a material weakening around its periphery which is dimensioned in such a way that when pressure is applied by the pin 20 it tears like a pre-determined breaking point over a substantial region of its periphery, but forms a hinge on one side. In this way the openable catch 19 is caused to open like a flap.

FIGS. 2 to 5 further show a condensate-binding device arranged in the chamber 14 consisting of two open-pored, absorbent sponges 21*a* and 21*b*. The sponges 21*a* and 21*b* absorb into their pores condensate deposits formed from the vapor phase and prevent freely mobile accumulations of condensate from forming in the inhaler component, in particular in the chamber 14, which could impair the function of the inhaler component and, in addition, could represent a risk for the user and the environment, if these accumulations contained drug residues or poisons such as nicotine. The two sponges 21*a* and 21*b* to a large extent line the inner walls of the chamber 14, where the sponge 21*a* extends up to the outlet of the air intake opening 15. In this way the condensate deposits should be prevented from reaching the relatively narrow slot-shaped air intake opening 15, as a result of which the air flow could be obstructed. In an alternative arrangement the air intake opening 15 could also be formed directly by the sponges 21*a* and 21*b*. The sponges 21*a* and 21*b* preferably consist of fine-pored, highly porous fiber composites. The company Filtrona Richmond Inc., www.filtronaporoustechnologies.com, specializes in the production of such fiber composites, in which both triacetin-bonded cellulose acetate fibers and thermally bonded polyolefin and polyester fibers are used.

As shown in FIGS. 2 to 3, a cooler 22 is provided downstream of the sponges 21*a* and 21*b*, which in the specific embodiment is integrated into the preferably interchangeable mouthpiece 3 and consists of a porous wadding 23, through the pores of which the vapor-air mixture or/and condensation aerosol formed flow. The cooler 22 cools the vapor-air mixture or/and condensation aerosol flowing through it and during this withdraws still further condensate from it. In this way the organoleptic characteristics of the vapor-air mixture or/and condensation aerosol taken up by the user can be significantly improved. The wadding 23 can consist for example of a tobacco filling. Such a tobacco filling additionally produces a flavoring of the vapor-air mixture or condensation aerosol flowing through it and is particularly desirable if the liquid material 13 contains nicotine.

Finally, it should be pointed out that the invention is naturally not limited to a laminar composite 5 in accordance with the embodiments just described. The composite could just as well have a linear format.

Furthermore, the composite could also be formed from a plurality of composites or composite sections arranged next to one another, where it is immaterial how the individual composites or composite sections are electrically interconnected to one another. In this connection it should be noted that by means of the multilayer printed circuit board 4 according to the invention both series connections and parallel connections as well as more complex wiring and actuation arrangements can be effected. Finally, the invention also covers devices in which the heating element is arranged separate from the wick. For example, the wick could be formed as a laminate and the heating energy transferred to the wick by electromagnetic waves, in particular radiant heat or microwaves.

LIST OF REFERENCES 1 snap connection
2 housing
3 mouthpiece
4 carrier plate, printed circuit board
5 laminar composite
6 heating element, resistance heating element
7 wick
7*a*, 7*b* end sections of the wick or composite
8*a*, 8*b* plug contacts
9 upper section
10 recess
11*a* first capillary gap
11*b* second capillary gap
11*c* third capillary gap
12 liquid container
12*a* first liquid container
12*b* second liquid container
13 liquid material
14 chamber
15 air intake opening
16*a*, 16*b* ventilation slots
17*a*, 17*b* ventilation holes
18*a*, 18*b* connecting channels
19 openable catch
20 pin
21*a*, 21*b* sponges
22 cooler
23 wadding

The invention claimed is:

1. An inhaler component comprising:
   a mouthpiece;
   a heating element configured to evaporate a portion of a liquid material;
   a liquid container for retaining the liquid material, the liquid container comprising a valve positioned on an interior face of the inhaler component, wherein the valve seals the liquid material within the liquid container; and
   a wick configured to automatically supply the liquid material to the heating element.

2. The inhaler component according to claim 1, wherein the valve hermetically seals the liquid within the liquid container.

3. The inhaler component according to claim 1, wherein the valve is located on a front face of the liquid container.

4. The inhaler component according to claim 1, wherein the valve has a material weakening around its periphery.

5. The inhaler component according to claim 1, wherein the valve forms a hinge on one side.

6. The inhaler component according to claim 1, wherein the valve is openable like a flap.

7. The inhaler component according to claim 1, further comprising a gap configured to automatically supply the wick with the liquid material, wherein the gap is a capillary gap and is further configured to automatically resupply the wick with the liquid material after evaporation.

8. The inhaler component according to claim 7, further comprising a laminar composite including the heating element and the wick, and configured such that liquid in the gap is transferred to the wick via an end section of the laminar composite.

9. The inhaler component according to claim 7, wherein the wick includes a first end section, a second end section, and an intermediate section between the first end section and the second end section, the gap configured to supply the liquid material to at least a portion of at least one of the first end section, the second end section, and the intermediate section.

* * * * *